(12) United States Patent
Yasinski et al.

(10) Patent No.: US 11,878,125 B2
(45) Date of Patent: Jan. 23, 2024

(54) RESPIRATORY THERAPY

(71) Applicant: YASI'S, LLC, Nampa, ID (US)

(72) Inventors: Jacob Lee Yasinski, Delburne (CA); Leo James Yasinski, Caldwell, ID (US)

(73) Assignee: YASI'S, LLC, Nampa, ID (US)

(*) Notice: Subject to any disclaimer, the term of this patent is extended or adjusted under 35 U.S.C. 154(b) by 493 days.

(21) Appl. No.: 16/646,283

(22) PCT Filed: Oct. 3, 2018

(86) PCT No.: PCT/US2018/054096
§ 371 (c)(1),
(2) Date: Mar. 11, 2020

(87) PCT Pub. No.: WO2019/070804
PCT Pub. Date: Apr. 11, 2019

(65) Prior Publication Data
US 2020/0282173 A1 Sep. 10, 2020

Related U.S. Application Data
(60) Provisional application No. 62/567,554, filed on Oct. 3, 2017.

(51) Int. Cl.
*A61M 16/20* (2006.01)
*A61M 15/00* (2006.01)
(Continued)

(52) U.S. Cl.
CPC ........ *A61M 16/208* (2013.01); *A61M 15/009* (2013.01); *A61M 15/0021* (2014.02); *A61M 16/0006* (2014.02); *A61M 16/0833* (2014.02)

(58) Field of Classification Search
CPC . A63B 23/18; A61M 16/0006; A61M 16/205; A61M 16/208
See application file for complete search history.

(56) References Cited

U.S. PATENT DOCUMENTS 5,451,190 A * 9/1995 Liardet ............ A61M 15/0015
482/13
6,539,937 B1 4/2003 Haveri
(Continued)

FOREIGN PATENT DOCUMENTS

WO WO 2016/142773 A2 9/2016

OTHER PUBLICATIONS

PCT Application No. PCT/US18/54096 Filing date Oct. 3, 2018; Jacob Lee Yasinski International Search Report, dated Feb. 8, 2019; 17 Pages.

*Primary Examiner* — Elliot S Ruddie
(74) *Attorney, Agent, or Firm* — Thorpe North & Western, LLP.

(57) ABSTRACT

Respiratory therapy devices, oscillating positive expiratory pressure assemblies, respiratory therapy assembly kits, and methods of respiratory treatment or therapy are disclosed. An example respiratory therapy device can include an airflow mixing channel including a first inflow opening, a second inflow opening, and an outflow opening. The device can further include a nebulizer fluidly coupled to the first inflow opening. A one-way air intake valve fluidly can be coupled to the second inflow opening and/or a one-way medicament valve fluidly coupled to the outflow opening. The respiratory therapy device can also include an oscillating positive expiratory pressure assembly fluidly coupled to the one-way medicament valve, wherein the oscillating positive expiratory pressure assembly includes a mouthpiece opening and an oscillatory valve. In certain specific examples, the one-way air intake valve or the one-way medicament valve can be an inhalation oscillatory valve.

23 Claims, 10 Drawing Sheets

(51) Int. Cl.
*A61M 16/00* (2006.01)
*A61M 16/08* (2006.01)

(56) References Cited

U.S. PATENT DOCUMENTS

| | | |
|---|---|---|
| 2003/0226562 A1 | 12/2003 | Schmidt et al. |
| 2012/0097164 A1 | 4/2012 | Rozario et al. |
| 2013/0228174 A1* | 9/2013 | Guo ................. A61M 16/0006 |
| | | 128/205.24 |
| 2013/0284171 A1* | 10/2013 | Adam .................. A61M 16/14 |
| | | 128/204.18 |
| 2014/0150801 A1* | 6/2014 | Rusher ............... A63B 21/0088 |
| | | 128/207.16 |

* cited by examiner

```
200
 ↓

┌─────────────────────────────────────────┐
│ delivering an aerosolized medicament to an airflow │──210
│ mixing channel prior to inhalation by a user │
└─────────────────────────────────────────┘
                    │
┌─────────────────────────────────────────┐
│ flowing air through a one-way air intake valve into │──220
│ the airflow mixing channel to mix with the │
│ aerosolized medicament and form a diluted │
│ aerosolized medicament │
└─────────────────────────────────────────┘
                    │
┌─────────────────────────────────────────┐
│ flowing the diluted aerosolized medicament through │──230
│ a one-way medicament valve and into lung airways │
│ of the user │
└─────────────────────────────────────────┘
                    │
┌─────────────────────────────────────────┐
│ flowing exhaled air from the user through an │──240
│ oscillatory valve │
└─────────────────────────────────────────┘
```

FIG. 16

RESPIRATORY THERAPY

The present application is a National Stage of International Application No. PCT/US2018/054096, filed on Oct. 3, 2018, which claims the benefit of U.S. Application No. 62/567,554, filed on Oct. 3, 2017,each of which are incorporated herein by reference in its entirety.

BACKGROUND

Respiratory diseases and disorders, such as chronic obstructive pulmonary disease (COPD), asthma, emphysema, bronchitis, bronchiectasis, fibrosis, sarcoidosis, alveolar damage, pleural effusion, or the like, can be treated with various methodologies. However, often these treatments come with undesired side effects and/or can be very time consuming. For example, COPD and other similar conditions can be treated with oral medications to reduce inflammation and/or suppress the immune system. However, there can be side effects with oral therapy because they are delivered systemically rather than more locally. Pulmonary rehabilitation is another treatment option but is more of a life-long strategy rather than a medicinal treatment, e.g., exercise training, nutritional counseling, education related to the disease and management of the disease, energy-conserving techniques and breathing strategies, psychological counseling, etc. Oxygen therapy can be used as well, but can require carrying equipment around which is inconvenient. As a last option, with some of the more severe diseases, a lung transplant can also be used as a treatment method.

BRIEF DESCRIPTION OF THE DRAWINGS

Additional features and advantages of the disclosure will be apparent from the detailed description which follows, taken in conjunction with the accompanying drawings, which together illustrate, by way of example, features of the present technology.

FIG. 16 is a flow diagram that graphically depicts an example method of treating a respiratory disease or condition in accordance with the present disclosure;

DETAILED DESCRIPTION

Figure 1:
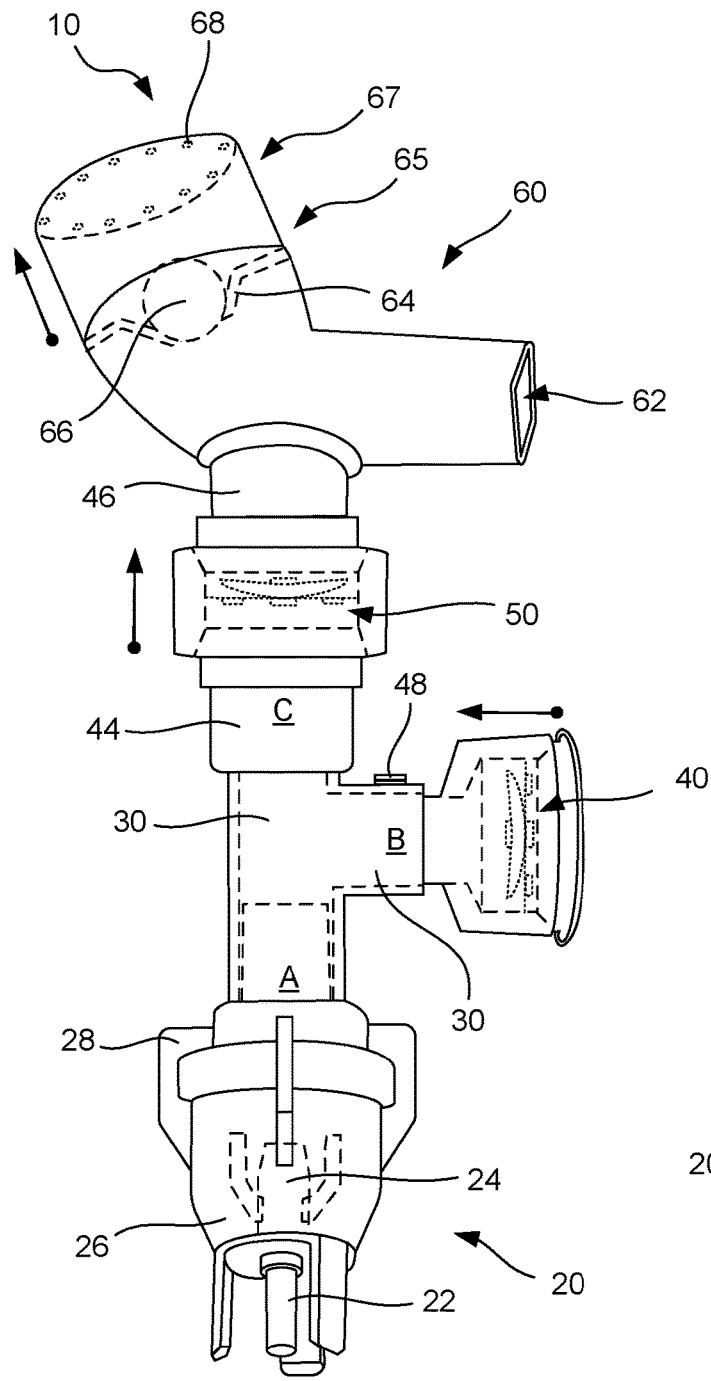
FIG. 1 is a side perspective view of an example respiratory therapy device in accordance with the present disclosure.

With some of the drawbacks related to various treatment options for pulmonary diseases or conditions, many patients have opted for a more localized medicinal application directly to the lungs. Furthermore, physiotherapies can also contribute to increased pulmonary health with few drawbacks. In accordance with this, the present disclosure is drawn to respiratory therapy devices and methods of treating respiratory diseases or conditions. In one example, a respiratory therapy device can include an airflow mixing channel including a first inflow opening, a second inflow opening, and an outflow opening. The respiratory therapy device can also include a nebulizer fluidly coupled to the first inflow opening, a one-way air intake valve fluidly coupled to the second inflow opening, and a one-way medicament valve fluidly coupled to the outflow opening. The respiratory therapy device can also include an oscillating positive expiratory pressure assembly fluidly coupled to the one-way medicament valve, wherein the oscillating positive expiratory pressure assembly includes a user-interface opening and an oscillatory valve. In one example, the oscillatory valve can also be a one-way valve that only allows airflow in a direction from within the oscillating positive expiratory pressure assembly to outside of the oscillating positive expiratory pressure assembly. As a note, the term "one-way" indicates the direction of fluid flow (e.g., gas, air, aerosolized droplets, etc.) as further informed by its coupling to its associated airflow mixing channel opening. For example, the one-way air intake valve is associated with the second "input" opening, and thus, the one-way valve would allow airflow into the airflow mixing channel, but not out. Likewise, the one-way medicament valve is associated with the "output" opening, and thus, the one-way valve would allow fluid flow (air and aerosolized liquid medicament) out of the airflow mixing channel, but not back in.

In another example, a method of treating a respiratory disease or condition can include delivering an aerosolized liquid medicament to an airflow mixing channel prior to inhalation by a user; flowing air through a one-way air intake valve into the airflow mixing channel to mix with the aerosolized liquid medicament and form a diluted aerosolized liquid medicament; and flowing the diluted aerosolized liquid medicament through a one-way medicament valve and into lung airways of the user. An additional step can include flowing exhaled air from the user through an oscillatory valve.

In another example, an oscillating positive expiratory pressure assembly can include an inhalation oscillatory valve, an exhalation oscillatory valve, and a user-interface opening in fluid communication with the inhalation oscillatory valve and the exhalation oscillatory valve. Thus, upon inhalation by a user, the inhalation oscillatory valve provides a first frequency response and the exhalation oscillatory valve is closed. Also, upon exhalation by the user the exhalation oscillatory valve provides a second frequency response and the inhalation oscillatory valve is closed.

In another example, a method of treating a respiratory disease or condition can include flowing air into lung airways of a user through an inhalation oscillatory valve actuated by user inhalation and generating a first frequency response, and flowing exhaled air from the lung airways of the user through an exhalation oscillatory valve actuated by user exhalation and generating a second frequency response. In this example, when the inhalation oscillatory valve is generating the first frequency response the exhalation oscillatory valve is closed, and when the exhalation oscillatory valve is generating the second frequency response the inhalation oscillatory valve is closed.

In another example, a respiratory therapy device can include a nebulizer, an inhalation oscillatory valve, and an exhalation oscillatory valve. A user-interface opening can be in fluid communication with the inhalation oscillatory valve and the aerosolized liquid medicament during inhalation, and in fluid communication with an exhalation oscillatory valve during exhalation.

In another example, a method of treating a respiratory disease or condition can include inhaling an aerosolized liquid medicament into lung airways of a user, wherein the inhaling also actuates an inhalation oscillatory valve. The method can also include exhaling air from the lung airways of the user through an exhalation oscillatory valve actuated by the exhalation.

In another example, a respiratory therapy kit can include an airflow mixing channel including a first inflow opening, a second inflow opening, and an outflow opening. The kit can also include a mouthpiece including an inhalation opening, a user-interface opening, and an exhalation opening. In this example, a plurality of one-way valves can be interchangeably fluidly couplable to the airflow mixing channel and the mouthpiece to provide one-way airflow from the outflow opening (of the airflow mixing channel) into the inhalation opening (of the mouthpiece) when a one-way valve of the plurality of one-way valves is fluidly coupled therebetween.

In still another example, a respiratory therapy kit can include a mouthpiece including an inhalation opening, a user-interface opening, and an exhalation opening. The mouthpiece can be an oscillating positive expiratory pressure assembly and the exhalation opening can be fluidly associated with an exhalation oscillatory valve. The kit can include a second mouthpiece including a second inhalation opening, a second user-interface opening, and a second exhalation opening. A one-way valve can be interchangeably fluidly couplable to the inhalation opening of the mouthpiece and the second inhalation opening of the second mouthpiece to provide one-way airflow into the mouthpiece or the second mouthpiece fluidly when fluidly coupled together.

In certain specific examples of the present disclosure, with respect to the respiratory therapy device described above and in the FIGS. below, when a user inhales through the user-interface opening, aerosolized liquid medicament formed at the nebulizer can admix with air brought in through the one-way air intake valve to form a diluted aerosolized liquid medicament in the airflow mixing channel. Furthermore, also when the user inhales, the diluted aerosolized liquid medicament can also pass through the one-way medicament valve and into the oscillating positive expiratory pressure assembly to be channeled out of the user-interface opening (and into the lung tissue of the patient). Furthermore, when a user exhales (after receiving the diluted aerosolized liquid medicament), exhaled air of the user enters the user-interface opening and exits through the oscillatory valve, but because of the one-way medicament valve, the exhaled air is not permitted to re-enter the airflow mixing channel. Prior to inhalation (or between inhalations), the airflow mixing channel also acts as an aerosolized liquid medicament storage chamber or channel. Thus, the aerosolized liquid medicament can be built-up and stored in the airflow mixing channel until inhalation, where the stored aerosolized liquid medicament mixes with inflowing air, and the diluted aerosolized liquid medicament is passed through the one-way medicament valve and delivered to the user's lung tissue.

In accordance with these and other examples, it is understood that the term "airflow" herein refers to the movement of gaseous fluid through the various fluid-directing parts, e.g., mouthpieces, oscillating positive expiratory pressure assemblies, one-way medicament valves, fluid-directing pivot joints, airflow mixing channels, one-way air intake valves, etc. It is thus explicitly understood that the term "airflow" includes not only the movement of air, but air carrying aerosolized medicament therewith. Also, in some examples, the general term airflow includes the flow of oxygen, an oxygen-rich gas mixture, or other gas or gas mixture that may be therapeutically helpful to a patient or user. Thus the term "airflow" should not be broadly interpreted as meaning flow of not only ambient air, but also any breathable gas or mixture, air carrying aerosolized medicament, or any other breathable gas or gas mixture that may also carry an aerosolized medicament, for example.

With respect to the various examples described herein that deliver an aerosolized medicament, including the respiratory therapy devices, oscillating positive pressure assemblies, respiratory therapy assembly kits, methods of treating respiratory diseases or conditions, or other devices, systems, assemblies, kits, methods, etc., there are various liquid medicaments that can be aerosolized and used in accordance with the present disclosure. Example aerosolizable liquid medicaments that can be used include various liquids, solutions, or dispersions of albuterol, accuneb, acetylcysteine, brovana, budesonide, cromolyn sod, duoneb, hypertonic-saline, ipratropium, levalbuterol, nebupent, perforomist, pulmicort, pulmozyme, sod chloride, tobramycin, tyvaso, ventavis, xopenex, foradil, formeterol, alformeterol, or a combination thereof in any pharmaceutically acceptable form.

It is noted that when discussing respiratory therapy devices, oscillating positive expiratory pressure assemblies, respiratory therapy assembly kits, or methods of treating a respiratory disease or condition, each of these discussions can be considered applicable to the other embodiment whether or not that feature is explicitly discussed in the context of the other example. To illustrate, in discussing a one-way medicament valve related to a respiratory therapy device, that same discussion regarding the one-way medicament valve can also be relevant and directly supportive of the method of treatment, and vice versa. As a further example, when discussing an inhalation oscillatory valve as the one-way medicament valve, any respiratory therapy device or method in the present disclosure can be understood to implement the inhalation oscillatory valve as the one-way medicament valve, whether specifically described in that context or not.

Figure 2:
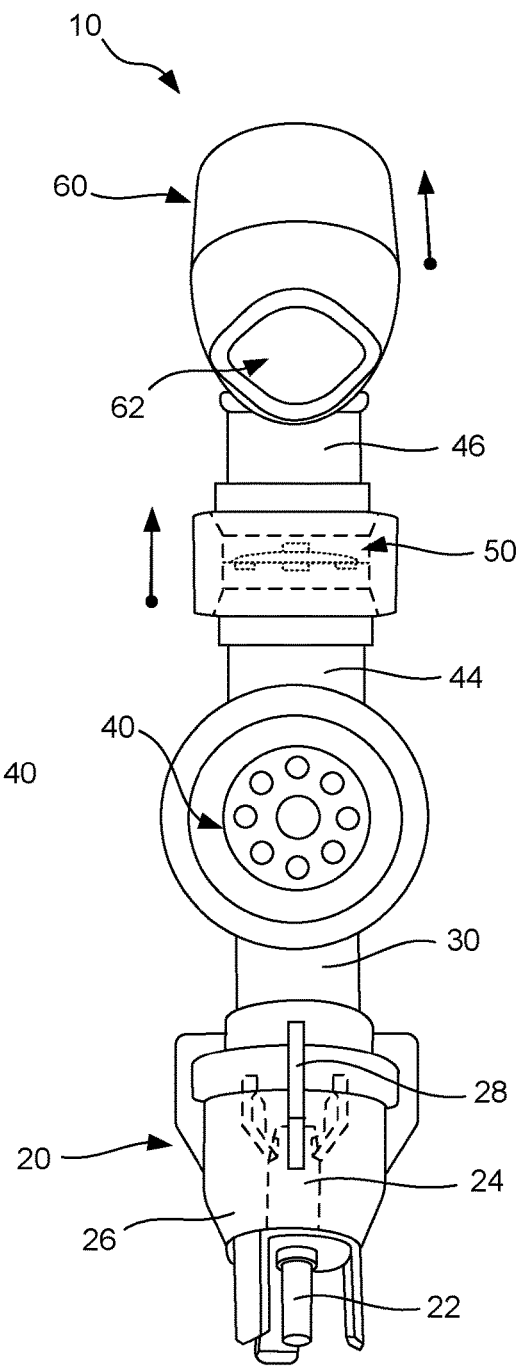
FIG. 2 is a front perspective view of the respiratory therapy device of FIG. 1.

Turning now to the FIGS., FIGS. 1 and 2 represent two different views of an example respiratory therapy device 10, namely a side perspective view and a front perspective view, respectively. The respiratory therapy device generally includes a nebulizer 20, an airflow mixing channel 30, and an oscillating positive expiratory pressure assembly 60, referred to herein alternatively as an "oscillating PEP assembly" or as an "OPEP assembly." The respiratory therapy device can further include multiple valve couplers 44, 46, which may be used to couple certain structures together, but such couplers may or may not be present, depending on how the various devices are assembled. Also, as shown in the FIGS., a one-way air intake valve 40, a one-way medicament valve 50, and an oscillatory valve 65 (which is also a one-way valve in this example) can be present, as will be described in greater detail hereinafter. In further detail regarding the airflow mixing channel, in this example, there are three openings, A, B and C. As a note, these openings are named as they relate to the airflow mixing channel, and thus inflow and outflow are described with respect to the direction of fluid flow into and out of the airflow mixing channel. Thus, a first inflow opening, or opening "A," is where the nebulizer delivers aerosolized liquid medicament into the airflow mixing channel. A second inflow opening, or opening "B," is where outside air is brought into the airflow mixing channel for mixing with the aerosolized liquid medicament, thereby forming a diluted aerosolized liquid medicament (aerosolized liquid medicament admixed with additional air). An outflow opening, or opening "C," is where the diluted aerosolized liquid medicament leaves the airflow mixing channel for inhalation by a device user. The second inflow opening (B) is fluidly associated with the one-way air intake valve. Thus, air is allowed in, but aerosolized liquid medicament is not allowed to escape at this location. Furthermore, the outflow opening (C) is fluidly associated with the medicament one-way valve. Thus, the diluted aerosolized liquid medicament can pass through the one-way medicament valve for delivery to the user, and upon exhaling by the user, the one-way medicament valve prevents exhaled air from the user to enter the airflow mixing channel.

In one example, the one-way air intake valve and/or the one-way medicament valve can be a one-way rubber stopper valve, such as that shown in FIGS. 1 and 2 generally at 40 and 50, respectively. More specifically, FIG. 1 shows the one-way rubber stopper valves in an open position for air inhalation (and the oscillatory valve 65 in a closed position), and FIG. 2 shows the one-way rubber stopper valves in a closed position during exhalation (with the oscillatory valve in an open oscillating configuration, not shown in FIG. 2, but shown in FIG. 3). In another example, the one-way air intake valve and/or the one-way medicament valve can also be an (inhalation) oscillatory valve, such as that shown at 65A in FIG. 10, for example. The use of an (inhalation) oscillatory valve at the one-way air intake valve or the one-way medicament valve location can provide the added benefit of loosening respiratory secretions during inhalation in addition to the loosening and removal that can also occur during exhalation through the (exhalation) oscillatory valve 65. Other types of one-way valves that can be used at either location include a diaphragm valve, a spring valve, a needle and seat valve, a butterfly valve with stopper, a swinging flapper valve, or the like, for example. In further detail, the airflow mixing channel can be configured to be a user handle for holding and manipulating the respiratory therapy device. In further detail, as shown in this example, the nebulizer, the airflow mixing channel, the one-way valves, the OPEP assembly, and optional couplers, are connected together without intervening narrow tubing, and thus, the device as a whole can be held as a unitary rigid structure rather than as multiple structures fluidly coupled together with narrow flexible tubing, etc. Thus, in one example, a user can handle the airflow mixing channel to manipulate the entire respiratory therapy device due to its rigid, unitary construction.

In further detail, there may be circumstances where pressure builds within the airflow mixing channel 30, and this pressure build up may be controlled by a pressure release valve or a pressure equalizing port 48, for example. This can be particularly an issue when the nebulizer is a jet nebulizer or atomizer where pressurized gas is used to form the aerosolized liquid medicament. In other words, since the airflow mixing channel typically acts as a closed system until user inhalation, there may be circumstances where a relatively long period of time between sequential inhalations occurs, e.g., 10 seconds, 1 minute, 5 minutes, etc. In this specific example, as mentioned, a pressure release valve or pressure equalizing port may be included that is pressure sensitive and allows for some outgassing to occur as may be appropriate in between inhalations. This valve or port can be positioned anywhere from the nebulizer cup 26 (above where the liquid medicament is filled) to the one-way medicament valve 50. In this example, the valve or port is shown through a side wall of the airflow mixing channel. In another example, alternatively, the one-way medicament valve itself can be configured to allow for some outgassing into the oscillating PEP assembly when the pressure reaches a certain threshold. Because the one-way medicament valve allows for fluid flow out of the airflow mixing channel, this valve may be available for outgassing. In still another example, another way to control pressure build up in the airflow mixing channel is to design or use an airflow mixing channel that is large enough in volume to handle pressure build up in between sequential inhalations by the user. Each time the user inhales, pressure build up can be essentially relieved, and thus, the relative large size of the airflow mixing channel (compared to the typical volume used in a nebulizer) can act as a buffer for expected pressure build up between even long respiration cycles or predictable non-use, e.g., temporarily putting the device down while allowing the nebulizer to continue to generate aerosolized liquid medicament.

In accordance with this, in one example, the airflow mixing channel can have a volume of about 15 cubic centimeters (cc) to about 150 cc, from about 30 cc to about 150 cc, from about 35 cc to about 100 cc, from about 40 cc to about 75 cc, from about 75 cc to about 150 cc, from about 15 cc to about 50 cc, from about 20 cc to about 40 cc, from about 22 cc to about 30 cc, or from about 15 cc to about 25 cc. In further detail, the nebulizer may include a nebulizer chamber (location where aerosolized liquid medicament is formed assuming no liquid medicament is present in the cup) volume from about 15 cc to about 80 cc, from about 20 cc to about 60 cc, from about 25 cc to about 50 cc, or from about 30 cc to about 40 cc, for example. One specific class of jet nebulizer can have a volume of about 25 cc to about 40 cc, for example. Other nebulizer chamber volumes can also be implemented for use in accordance with examples of the present disclosure, depending on the specific model and/or type of nebulizer. In further detail, the volume ratio of a nebulizer chamber to airflow mixing channel can be from about 2:1 to about 1:10, from about 1:1 to about 1:10, from about 1:1.2 to about 1:5, or from about 1:1.3 to about 1:3, for example. Thus, the airflow mixing channel can at least double the volume of the available volume for the aerosolized liquid medicament to flow prior to passing through the one-way medicament valve (mixed with air flowing in through the one-way air intake valve). As a note, in examples where there is not a one-way medicament valve present, the available volume that is doubled is that which occurs prior to entering the oscillating positive expiratory pressure assembly 60.

When calculating volumes of the airflow mixing channel 30, there can be some difference between the volume within the structure itself and the total volume where airflow mixing occurs. Thus, for more precise measurements, the airflow mixing volumes are calculated to the volumes generally found between all three openings A, B, and C. However, depending on the one-way valves 40, 50 used, how the one-way valves are actually connected, more or less airflow mixing volume may be present. For example, in the example shown at FIGS. 1 and 2, there can be some additional airflow mixing volume provided by a portion of the housings used to support the one-way valve rubber stoppers. These additional volumes can be proximate to the airflow mixing channel structure per se, which is specificity shown at 30. To illustrate by exemplary numbers, the airflow mixing channel structure per se may be a T-shaped tube (as shown in FIGS. 1-2, but which can have other configurations, such as Y-shaped as shown in other FIGS.) that can have a total volume of about 15 cc to about 50 cc, from about 20 cc to about 40 cc, from about 22 cc to about 30 cc, or from about 15 cc to about 25 cc. The housing surrounding the one-way air intake valve 40 can provide an additional about 7 cc to about 25 cc of total volume, with about 5 cc to about 20 cc, about 5 cc to about 15 cc, or about 10 cc to about 15 cc of volume within the valve housing "after" or downstream from the rubber stopper valve portion, though these volumes are exemplary only. Furthermore, the housing surrounding the one-way medicament valve 50 can also provide an additional about 7 cc to about 25 cc of total volume, with about 5 cc to about 20 cc, about 5 cc to about 15 cc, or about 10 cc to about 15 cc of volume within the valve housing "after" or downstream from the rubber stopper valve portion, though these volumes are exemplary only. Thus, in all open volume portions of the "airflow mixing channel," the total mixing volume can be from about 20 cc to about 80 cc, from about 25 cc to about 60 cc, or from about 35 cc to about 55 cc. Again, these volumes are examples only and larger or smaller volumes can be used. This volume does not include the nebulizer chamber volume, which is the nebulizing volume that generates and feeds the aerosolized liquid medicament into the airflow mixing channel, and ultimately through the one-way medicament valve for user inhalation. Thus, when referring to an "airflow mixing channel," this refers to a structure similar to that shown at 30. However, when referring to an "airflow mixing channel volume" or "mixing channel volume" or "volume of the airflow mixing channel," or similar terminology, what is referred to is the total volume between the nebulizer (not including the nebulizing volume that feeds the airflow mixing channel), the one-way air intake valve, and the one-way medicament valve, regardless of what structure provides the volume to the calculation. The nebulizing volume in this example is shown terminating approximately where the nebulizer 20 connects to the airflow mixing channel 30. In one example, if one or both of the one-way valves is not present, then the volume is calculated to the opening of the airflow mixing channel structure, for example.

In further detail regarding the nebulizer 20 in FIGS. 1 and 2, it is understood herein that the term "nebulizer" is defined to include structures or devices configured to convert liquid medicament to aerosolized liquid medicament, but does not include any peripheral or ancillary equipment used to operate the nebulizer. For example, a gas compressor and hose for connecting the gas compressor to the nebulizer are not considered to be part of the nebulizer per se, but rather peripheral components used to operate the nebulizer. A power source used to power a piezoelectric transducer in an ultrasonic nebulizer is also not considered to be part of the nebulizer per se, but rather peripheral equipment used to operate the nebulizer. Likewise, the liquid medicament loaded in a nebulizer cup is also not part of the nebulizer as defined. FIGS. 1 and 2 show an example nebulizer which, in this embodiment, can include in its simplest form, a nebulizer cup 26 for holding liquid medicament, and a jetting device 24 with a nozzle(s) (not shown herein but shown in greater detail in FIG. 4) for jetting gas through the liquid medicament to generate an aerosolized liquid medicament. Other structures that can be present include a gas intake interface 22 (e.g., for connecting a separate gas line) and, in this example, handling wings 28 which can be present to assist with attaching the nebulizer device to other structures.

The use of a nebulizer 20 in conjunction with the oscillating positive expiratory pressure assembly 60 can be used to effectively treat any of a number of respiratory diseases or disorders, such as chronic obstructive pulmonary disease (COPD), asthma, emphysema, bronchitis, bronchiectasis, fibrosis, sarcoidosis, alveolar damage, pleural effusion, or the like. Delivering liquid medicament as an aerosolized droplet directly to the lungs can act to reduce inflammation, swelling, and/or mucus within the airways. For example, often corticosteroids and/or bronchodilators can be used to treat these and other diseases by directly delivering the aerosolized liquid medicament to lung tissue because, when administered in this manner, they can be more effective in directly treating the respiratory tract, often improving speed of delivery and reducing side effects. Furthermore, by combining this therapy with an OPEP assembly, the user can often experience deeper breathing for more effective treatment, shortened total therapy times, breakup of mucous in the lungs while medicine is being received during the same respiratory cycle, etc. All of these can have therapeutic benefits. Treatment time, droplet size, delivery efficiency, and other factors can have an impact on the therapeutic effect as well. For example, if a treatment typically lasts for 30 minutes to one hour for individualized nebulizer treatment, and then the medicine delivery is followed by OPEP assembly treatment (or vice versa) lasting from 30 minutes to one hour, by using the device of the present disclosure, the total treatment time might be from 20 to 30 minutes to one hour, rather than one hour to two hours. This reduced treatment time may be because of several factors other than combining simultaneous treatment. As mentioned, efficient medicine delivery with minimal wastage, as well as providing large air volume intake through the one-way air intake and medicament valves to promoting deeper breathing, may also partially contribute to reduced treatment times.

With more specific detail regarding the nebulizer 20, any of a number of nebulizers can be used in accordance with the present disclosure. For example, a soft mist inhaler can deliver a metered dose using manually rotated springs to build up tension around a flexible container and, when tension is released, pressure on the flexible container causes the liquid to be sprayed. This type of system does not require a gas propellant, such as pressurized air or oxygen, or a power source. Powered systems can include atomizers or jet nebulizers, ultrasonic wave nebulizers, or vibrating mesh nebulizers. A jet nebulizer or atomizer, as mentioned previously, delivers compressed or pressurized gas, e.g., air or oxygen, through a tube where it is jetted through a liquid medicament, usually held by a nebulizer cup, turning the liquid medicament into an aerosol just above the liquid medicament reservoir. Thus, when a jet nebulizer is used, in one example, the respiratory therapy device can further include a gas compressor fluidly coupled to the nebulizer for jetting a pressurized gas into the nebulizer for aerosolizing a liquid medicament. Suitable gasses can include oxygen, air, or other gases known for use with atomizers or jet nebulizers, for example. Thus, the gas compressor can be fluidly coupled to the nebulizer by a removable tube that attaches to the nebulizer, for example. An ultrasonic wave nebulizer, on the other hand, can alternatively be used and utilizes an electronic oscillator to generate a high-frequency ultrasonic wave. The mechanical vibration produced can be from a piezoelectric element, for example, which contacts the liquid medicament, thereby forming a vapor. A vibrating mesh nebulizer can also be used and this type of device creates a mist though very small holes that vibrate at or near a liquid reservoir. As the mesh vibrates, the liquid can become aerosolized. Any of these types of nebulizers, or others, can be used in accordance with examples of the present disclosure.

As mentioned, in addition to treating various respiratory diseases with aerosolized medicine, physiotherapies can be carried out using certain medical devices that assist with improving respiratory conditions. For example, there are many respiratory diseases or conditions that can interfere with mucociliary clearance, and certain breathing apparatuses can facilitate the loosening and removal of unwanted respiratory system secretions. One type of device that can be used is an oscillating positive expiratory pressure (OPEP) device 60 which provides high-frequency airflow oscillation or vibration suitable for mobilizing and expectorating mucus, for example. In the example shown in FIGS. 1 and 2, the OPEP assembly includes a user-interface opening 62 for inhaling and exhaling by the user. The OPEP assembly also includes an oscillatory valve 65 which, in this example, includes a weighted ball 66 and valve seat 64 with an opening therein. A perforated cap or cage 67 allows exhaled air to escape (past the weighted ball), and the cap in this example can include a series of perforations 68. The airflow through the perforations or cage openings can contribute to the oscillating effect of the oscillatory valve, in some examples. Thus, in accordance with examples of the present disclosure, the oscillatory valve can include a weighted ball and a valve seat for receiving the weighted ball. In one example, a cage or perforated cover (or similar structure) can allow the weighted ball to oscillate above the valve seat without escaping and allow expiratory air to exit past the weighted ball and through openings of the cage or perforated cover of the oscillating positive expiratory pressure assembly.

One specific type of oscillating positive expiratory pressure (OPEP) device is known as the Flutter® Mucous Clearance Device, commercially available from VarioRaw Percutive S.àr.I., a subsidiary company of Aptalis Pharma US, Inc., Bridgewater, NJ. Essentially, the Flutter® includes a mouthpiece for exhaling respiratory air through a one-way valve that includes a cone shaped opening, a steel ball, and a cap with a series of perforations to hold the steel ball within a small area while letting air escape through an opening of the valve seat around the weighted ball, e.g., through the perforated cap. As the expiratory airflow passes through the device, the steel ball can become slightly raised above the cone opening causing the steel ball to vibrate within the device body, e.g., above the cone shaped opening and beneath the cap. The vibrating ball leads to respiratory airflow vibration/oscillation. The Flutter® device, however, is different than the OPEP assembly shown in FIGS. 1 and 2 in that the OPEP assembly of the present disclosure includes an opening through a wall thereof for receiving aerosolized liquid medicament for user inhalation. The commercially available Flutter® device does not include a similar opening adapted for receiving aerosolized liquid medicament via inhalation.

Turning now to FIG. 3, various fluids and fluid flow paths are shown in some detail using the respiratory therapy device 10 previously shown and described in FIGS. 1 and 2. However, it is understood that variously configured airflow mixing channels 30, various types of nebulizers 20, and/or various types of oscillating positive expiratory pressure assemblies 60 can be used with similar airflow patterns. That being stated, many of the structures shown in FIG. 3 are the same as those shown in FIG. 1 so specific descriptions of those structures are incorporated into the device shown in FIG. 3, whether or not specifically described in the context of FIG. 3.

Regarding the fluid flow paths, notably, there are multiple fluids shown in FIG. 3. For example, there is a flow path for compressed or pressurized gas 12, which can be pressurized oxygen or air, for example. In this example, the pressurized gas is generated using a compressor 70, and the pressurized gas is channeled through a flexible tubing 74 into a coupler 76 that attaches to the gas intake interface 22 of a nebulizer. The flexible tubing and the coupler can be referred to collectively as a removable tube. The compressor and the removable tube are considered peripheral equipment that is used with the nebulizer to generate aerosolized liquid medicament 25 from liquid medicament 21 held by a nebulizer cup 26 portion of the nebulizer. Essentially, the pressurized gas is ejected through a portion of the liquid medicament via jetting architecture 24. Further detail regarding the aerosolization of the medicament is shown and described in FIG. 4. Once the aerosolized liquid medicament is generated, it can then be delivered to the airflow mixing channel 30 for storage and then mixing with a separate inflow of air 36.

In further detail, the airflow mixing channel 30 provides a storage and channeling chamber for receiving multiple fluid flows, mixing those fluid flows together, and then delivering the mixture therefrom. More specifically, the aerosolized liquid medicament 25 is delivered from the nebulizer 20 to the airflow mixing channel where the aerosolized liquid medicament is mixed with air 36 to form a diluted aerosolized liquid medicament 29 within the airflow mixing channel. In further detail, the air is brought into the airflow mixing channel though a one-way air intake valve 40. By utilizing a one-way air intake valve, aerosolized liquid medicament wastage can be significantly reduced or even essentially eliminated. This is because air is allowed to flow into the airflow mixing channel for mixing with the aerosolized liquid medicament, but air and aerosolized liquid medicament are not allowed to escape the airflow mixing channel at this location.

One problem with certain nebulizers 20, particularly atomizers or jet nebulizers, is that they are typically designed to operate continuously during therapy. Thus, the pressurized gas 12, e.g., air or oxygen, typically continuously generate the aerosolized medicine 25, and is not normally switched off until the end of therapy. This can lead to fairly significant wastage of medicine. To illustrate, even though the nebulizer system is aerosolizing medicine continuously, the medicine is only available for inhalation while the patient is inhaling. As a result, in many systems, aerosol released and/or accumulated in the nebulizer system during exhalation can be wasted. This can be significant because the inhalation process only occupies about a third (⅓) of the respiratory cycle time in a human with normal lung function. Furthermore, for a user experiencing a respiratory disease, sometimes inhalation occupies less than a third of respiration cycle time. Thus, as much as two-thirds (⅔) of the medicinal aerosol that is available for inhalation becomes subject to evacuation from the device, either through expiration or through natural bleeding of the aerosolized liquid medicament from the device openings. This, in combination with other types of wastage that can occur at other locations within the nebulizer system, can result in a very large portion of the medicine going unused or rendered ineffective. By utilizing the one-way air intake valve, as mentioned, wastage while the aerosolized liquid medicament is being stored (awaiting an inhalation) can be ameliorated.

The diluted aerosolized liquid medicament 29, which includes a mixture of the aerosolized liquid medicament 25 and air 36, can then flow through a one-way medicament valve 50 for inhalation by a user 90 though a user-interface opening 62. In this manner, as the user inhales, the diluted aerosolized liquid medicament can be brought through the one-way medicament valve and into the lungs of the user. Furthermore, upon inhalation, the one-way air intake valve (and the one-way medicament valve) can be configured to allow for a full inhalation breath by the user so that the aerosolized liquid medicament can be deeply brought into the lung passages of the user.

After inhalation by the user 90, the user can then exhale through the same user-interface opening 62. Upon exhaling, the exhaled air 38 is then directed through another one-way valve which, in this instance, is an oscillatory valve 65. Thus, in this example, the exhaled air causes a weighted ball 66 to vibrate or oscillate over an opening of a valve seat 64 where the exhaled air can escape through a series of perforations 68 in its valve cap. Furthermore, because of the presence of the one-way medicament valve, the exhaled air is not allowed to re-enter or flow back into the airflow mixing channel, and thus, essentially the entire exhalation of the user is directed toward the oscillatory valve, which provides for a more efficient use of the oscillatory valve and general OPEP therapy.

In further detail regarding the one-way medicament valve 50, this valve can also provide the added benefit of further reducing aerosolized liquid medicament 25 waste. For example, under normal usage conditions, diluted aerosolized liquid medicament 29 is not typically allowed into the oscillating PEP assembly 60 unless the user 90 is inhaling. Furthermore, no more than a deminimis amount of aerosolized liquid medicament becomes evacuated upon expiration by the user. In other words, the only aerosolized liquid medicament that may be available for exhaling wastage would be aerosolized liquid medicament that was inhaled but not absorbed by the user, or the small amount of the aerosolized liquid medicament that may remain in OPEP airflow channel 69 at the trailing end of the inhalation cycle, i.e., the aerosolized liquid medicament that did not quite make it past the mouthpiece. This amount of waste is considered to be minimal. On the other hand, there may be essentially no wastage related to aerosolized liquid medicament passively bleeding into the OPEP airflow channel (unless the pressure is great enough in the airflow mixing channel to force aerosolized liquid medicament through the one-way medicament valve, which would be a fairly rare occurrence during normal use). Under normal operation, unless the user is inhaling, the aerosolized liquid medicament does not typically enter the OPEP airflow channel, and thus, the constant bleed of medicament is not particularly subject to exhalation waste.

Figure 3:
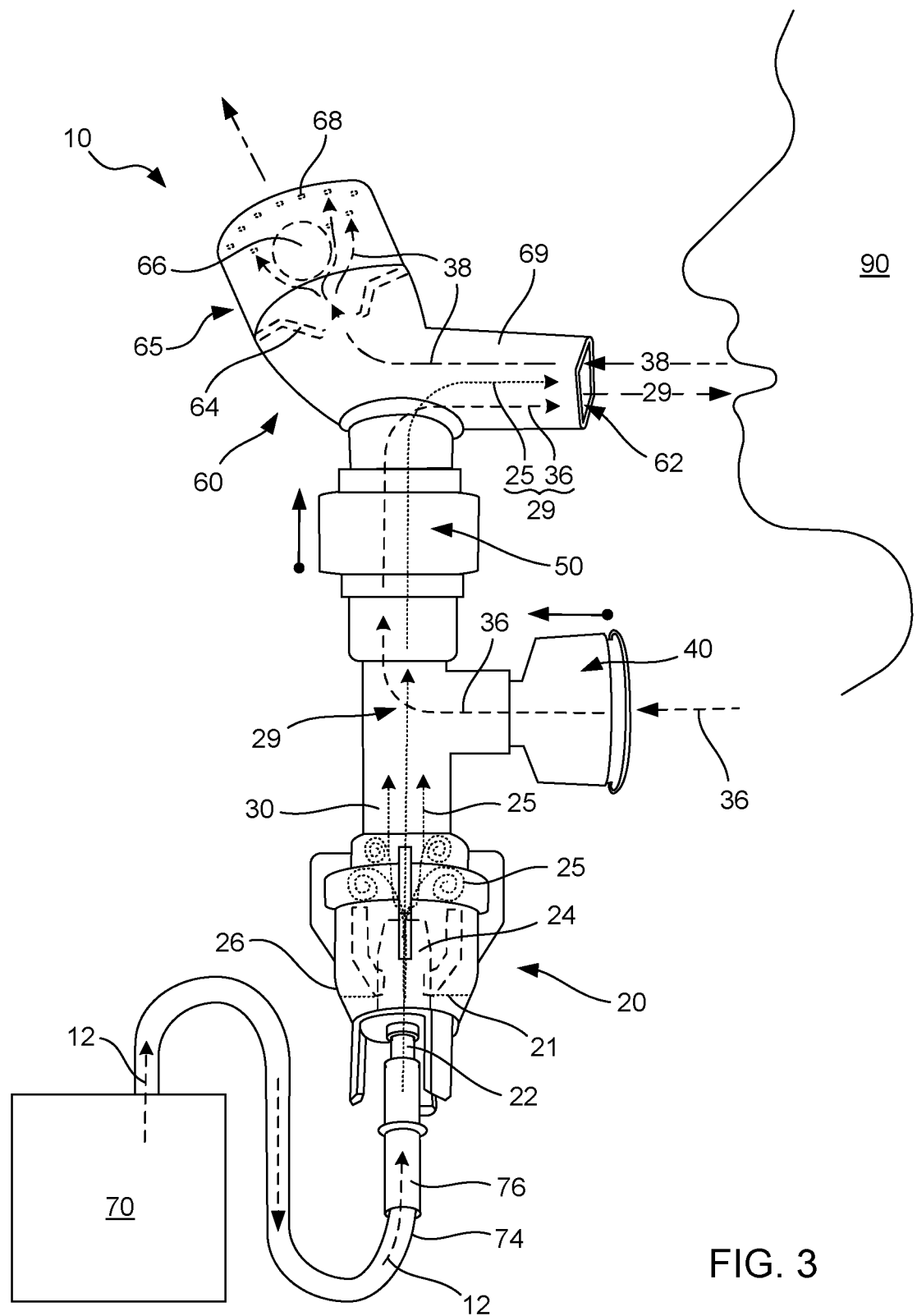
FIG. 3 is a side perspective view of an example respiratory therapy device similar to that shown in FIG. 1, but which further includes additional detail with respect to example compressor device attachment, example aerosol formation, example fluid flow pathways, example fluid mixing locations, example user interface, example oscillatory valve operation, etc., in accordance with the present disclosure.

In addition to this, there are other advantages to the fluid flow patterns shown and described with respect to FIG. 3. For example, as mentioned, the one-way air intake valve 40 can act to hold the aerosolized liquid medicament 25 or nebulizer vapors in the airflow mixing channel 30 during the entire respiratory cycle, even when opened during air inhalation due to the external airflow into the airflow mixing channel. In other words, either the one-way air intake valve is closed, or it is open and receiving air 36 during inhalation. Thus, no more than perhaps a deminimis amount of aerosolized liquid medicament can escape at this location. Furthermore, the atmospheric pressure drop that occurs during inhalation within the airflow storage chamber can cause a thorough mixing of the aerosolized liquid medicament upon a burst of the vapor being drawn from the nebulizer. Thus, the device can provide for efficient use of aerosolized liquid medicament or vapor while preventing an undue amount of medicament waste from escaping the airflow mixing channel, in addition to ameliorating other potential waste streams described herein.

Figure 4:
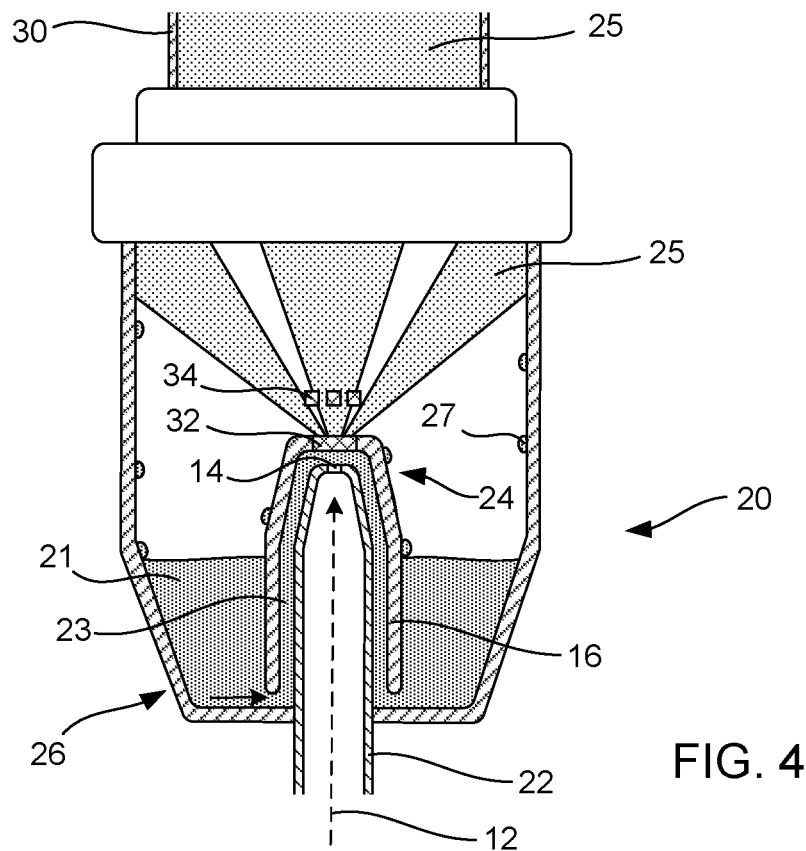
FIG. 4 is a cross-sectional view of an example jet nebulizer or aerosolizer which can be used with the example respiratory therapy devices of the present disclosure.
Figure 5:
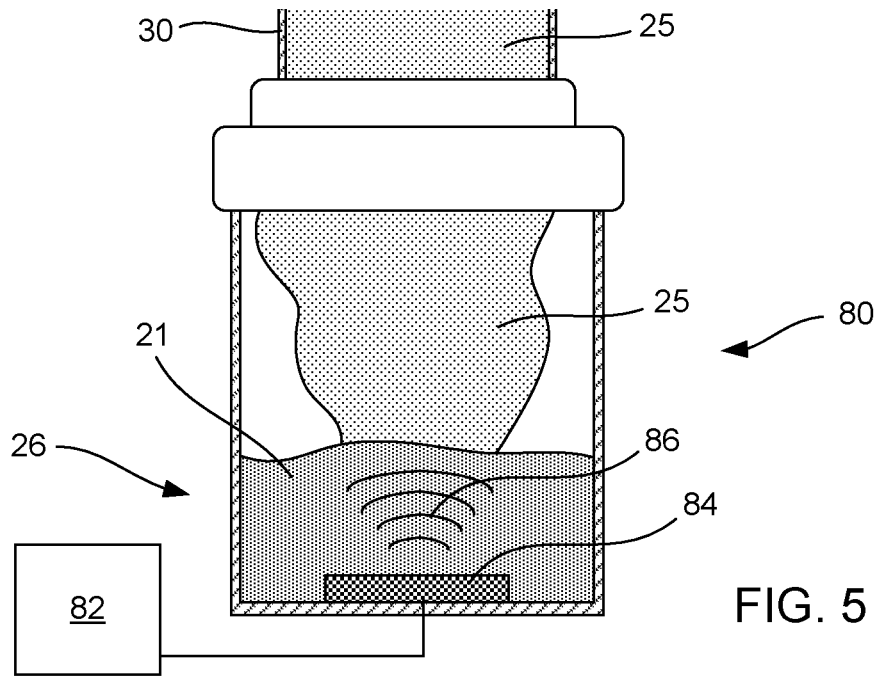
FIG. 5 is a cross-sectional view of an ultrasonic wave nebulizer which can be used with the example respiratory therapy devices of the present disclosure.

Turning now to FIGS. 4 and 5, two different types of nebulizers are shown that can be used in accordance with examples of the present disclosure, namely a jet nebulizer and an ultrasonic wave nebulizer. However, it is noted that other types of nebulizers can be used, such as manually operated nebulizers and vibrating mesh nebulizers, which are not specifically shown.

With specific reference to FIG. 4, a jet nebulizer 20 or atomizer is shown. The jet nebulizer can include a nebulizer cup 26 loaded with a liquid medicament 21. More specifically, in this example, a pressurized gas 12 is jetted through an aerosolizing or jetting architecture 24 to generate the aerosolized liquid medicament 25. The jetting architecture includes a liquid aspiration channel 23 (defined by an outer wall 16 and the gas intake interface 22) for drawing liquid medicament to a location adjacent to a pressurized gas jetting orifice or nozzle 14. Thus, as the pressurized gas is jetted through the nozzle and then through a thin layer of the liquid medicament, the liquid medicament can be converted from a liquid to the aerosolized liquid medicament. In this example, the aerosolization of the medicament can be assisted by the presence of one or more disruption member(s). In this example, two different types of disruption members are shown, namely a screen 32 and a series of baffles 34, though other structures alone or in combination can be used to assist in the formation of the aerosolized liquid medicament. In further detail, because jet nebulizers are not generally 100% efficient, some of the aerosolized liquid medicament may not form an aerosol and are thus returned or recycled to the nebulizer cup for further use. Furthermore, when the aerosolized liquid medicament contacts walls of the nebulizer, larger droplets of medicament 27 can be formed and likewise recycled back into the nebulizer cup. The recycling of medicament is not considered to be wastage in accordance with the present disclosure as it is recycled for further use. However, it is known that some nebulizer cups are not fully efficient and some liquid medicament may remain at the bottom of the nebulizer cup once the nebulizer stops generating aerosol vapor. That being understood, in vaporization or aerosolization, the nebulizer can then deliver the aerosolized liquid medicament to the airflow mixing channel 30 as previously described in connection with FIG. 3.

With specific reference to FIG. 5, an ultrasonic wave nebulizer 80 is shown. This type of nebulizer can be used in place of the jet nebulizer shown in FIGS. 1-4 and hereinafter in FIGS. 6 and 9, for example. The ultrasonic wave nebulizer can include a nebulizer cup 26 loaded with a liquid medicament 21. In this example, a power source 82 can be electrically coupled to a piezoelectric transducer 84 which, when activated by the power source, generates vibration waves 86 within the liquid medicament. The vibration waves cause a portion of liquid medicament at the surface to form an aerosolized liquid medicament 25. As with the jet nebulizer, aerosolized liquid medicament can be recycled by forming larger droplets (not shown, but shown in FIG. 4) that are returned to the liquid medicament reservoir. Furthermore, as with the jet nebulizer, the ultrasonic wave nebulizer can be configured to include disruption members (not shown), such as baffles or the like, for increasing the efficiency of the aerosolization process. Upon generating the aerosolized liquid medicament, the nebulizer can then deliver the aerosolized liquid medicament to the airflow mixing channel 30 as previously described in connection with FIG. 3.

Figure 6:
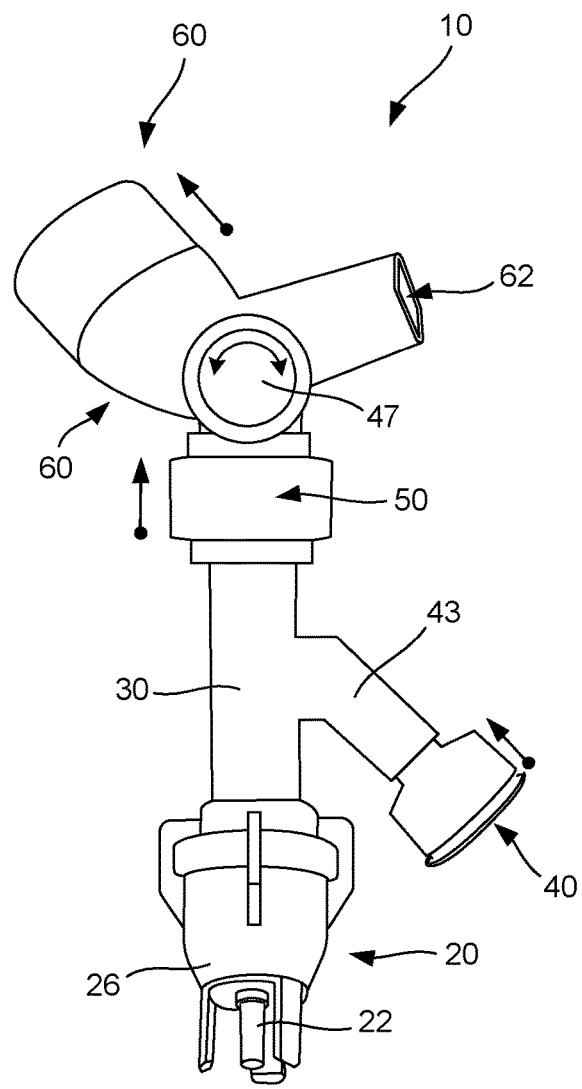
FIG. 6 is a side perspective view of an example respiratory therapy device similar to that shown in FIG. 1, but which includes an example tiltable oscillatory valve (carried out by tilting the entire oscillating positive expiratory pressure assembly in this example) and a modified airflow mixing channel in accordance with the present disclosure.
Figure 7:
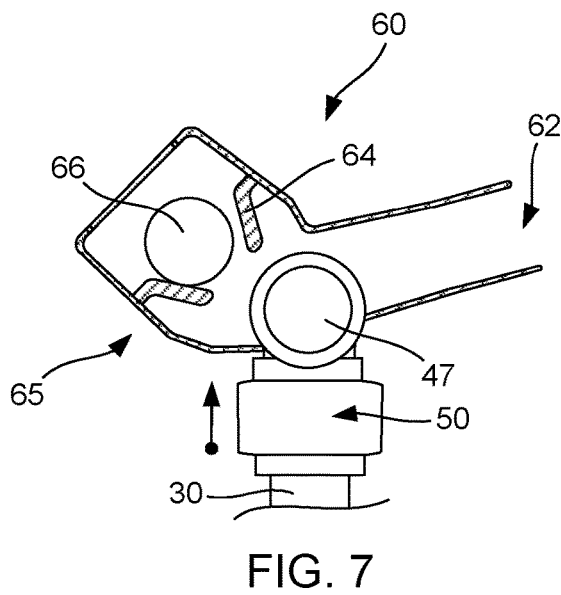
FIG. 7 is a partial cross sectional view of the oscillating positive expiratory pressure assembly of FIG. 6 pivoted or tilted downward for reducing the frequency response of the oscillatory valve in accordance with the present disclosure.
Figure 8:
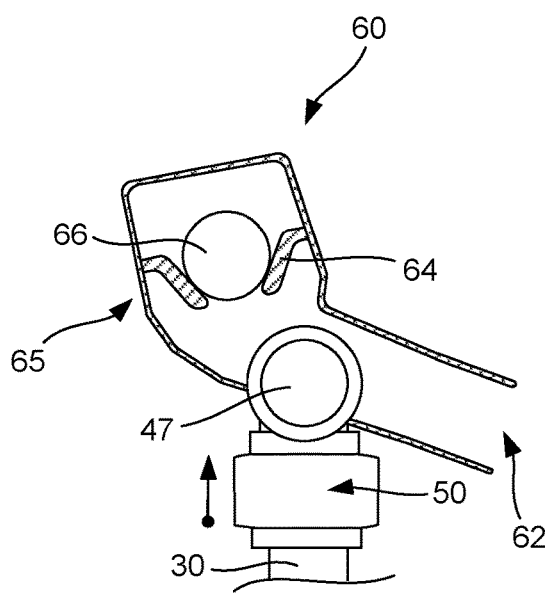
FIG. 8 is a partial cross sectional view of the oscillating positive expiratory pressure assembly of FIG. 6 pivoted or tilted upward for increasing the frequency response of the oscillatory valve in accordance with the present disclosure.

Various other modifications to the respiratory therapy device shown in FIGS. 1-3 can also be implemented in accordance with examples of the present disclosure. For example, as shown in FIGS. 6-8, the respiratory therapy device 10 can be adapted so that the angular relationship between the oscillating PEP assembly 60 (or at least the oscillatory valve 65) and the airflow storage device 30 (or the nebulizer) can be modified. For example, the oscillatory valve can be pivotable or tiltable with respect to the airflow mixing channel (or the nebulizer) using fluid-directing pivot joint 47, which in this example, is a hinged joint. The term "pivot joint" is to be interpreted broadly to include any type of movable joint, flexible material, or otherwise that would allow the angular relationship between two structures (or even the angular relationship between a single structure configured in a relative neutral or standard position) to be modified. Typically the fluid joint includes an internal channel that directs fluid flow, e.g., airflow, aerosolized medicament flow, etc., but the pivot joint could be mechanical in nature with fluid flow that bypasses the pivot joint, e.g., a mechanical pivot joint with tubing that bypasses the mechanical pivot joint. That being described, in the examples herein, the pivot joints that are shown are "fluid-directing pivot joints," meaning that they are both pivot joints for mechanical angle relationship modification, and they include an internal fluid flow channel that acts to direct airflow, medicament, etc., from one fluidic body to another. Thus, description here related to pivot joints explicitly includes as a species, fluid-directing pivot joints.

Typically, the modifiable angle relationship can remain stable until acted upon by a user to adjust the pivot joint. In further detail, the pivot joint is shown at an example location but could alternatively be positioned elsewhere on the respiratory therapy device, such as between the nebulizer and the airflow mixing channel, or between the user-interface opening 62 and the oscillatory valve, for example. Essentially, the pivot joint can be anywhere on the device where an angular relationship between the oscillatory valve and any other structure is present so that the valve can be angularly adjusted while allowing the other features of the respiratory therapy device to function properly and/or for ergonomic considerations. In one example, the oscillating PEP assembly (and thus the oscillatory valve) can be positioned in a neutral position with respect to the airflow mixing channel, such as that shown in FIG. 1, or in a downward angle with respect to the airflow mixing channel such as that shown in FIGS. 6 and 7, or in an upward angle with respect to the airflow mixing channel such as that shown in FIG. 8. Generally, by pivoting the angle of the oscillatory valve upward or downward, the user can match or otherwise adjust the vibration of the oscillatory valve to maximize (or modify for other reasons) the vibratory effect that the device has on that specific user's lungs. In further detail, as shown in FIG. 6, because the oscillating PEP assembly is attached to a nebulizer which contains a liquid medicament, adjusting the angle of the oscillatory valve (or the entire OPEP assembly portion) is not always as simple as merely tilting the entire respiratory therapy device as a whole, as such angling might also tilt the nebulizer in a manner that reduces its operability or efficiency, e.g., the nebulizer may work best when in a standard upright position. Thus, by adding the pivot joint as shown in FIG. 6, the nebulizer, for example, can remain in its standard upright position, and yet the oscillatory valve can be angularly adjusted as may be clinically most effective for a particular user.

In further detail regarding the modification of the angle at which the oscillatory valve 65 is positioned with respect to the airflow mixing channel 30 (or with respect to the upright position of the nebulizer 20, etc.), FIGS. 7 and 8 show the general position of the weighted ball 66 within the valve seat 64 and how modification of the angle using the pivot joint 47 can thus modify the valve frequency response and/or amplitude. Even without adjustability, amplified vibrations coupled with increased expiratory pressure can work together to lead to the loosening and removal of the unwanted respiratory system secretions via mucociliary clearance. With adjustability, the oscillatory valve can be tuned more carefully for an individual user. Essentially, by modifying the angle, the user can modify the force of exhaled respiratory air used to vibrate the weighted ball, thereby providing the user with some control of the oscillation, e.g., frequency response and amplitude. For example, as shown in FIGS. 6-8, the oscillatory valve can produce a range of oscillation frequencies from about 6 Hz and 20 Hz. This frequency response range can correspond to the range of the pulmonary resonance frequencies in humans. Achieving a resonance frequency suitable for treating a specific user can occur when the pressure becomes amplified, generating desirable vibrations at the target airway wall. In one specific example, the oscillating positive expiratory pressure assembly or oscillatory valve can be adjustable at an oscillation frequency range of from 6 Hz to 20 Hz, or at least from 10 Hz to 18 Hz. In one example, the oscillation frequency produced by the oscillatory valve can be about 15 Hz when in its neutral position, e.g., horizontal mouthpiece, as shown in FIG. 1. The frequency response can thus be modified by adjusting the angle from its neutral position. For example, by angling the device upward, a higher frequency response can be realized, and by angling the device downward, a lower frequency response can be realized. Thus, the patient can adjust the resonance frequency by simply selecting the angle or tilt of the device, e.g., greater than about 15 Hz, e.g., from >15 Hz to 20 Hz, by tilting upward or from less than about 15 Hz, e.g., <15 Hz to 6 Hz, by tilting downward. Furthermore, as can be seen in FIG. 7, when angled downward, a lower amount of airflow force may be enough to generate the vibratory effect, whereas in FIG. 8, because the weighted ball may be seated more fully in the seat valve, greater airflow may be needed to generated the vibratory effect. Thus, angling of the oscillatory valve using the pivot joint can adjust frequency response, amplitude, and/or mean airflow pressure. Regardless of the specific design, the oscillatory valve can be configured to have a different "neutral" frequency response value (other than about 15 Hz) when in the standard upright/neutral position, and adjustability can be based on whatever the frequency response is from the neutral position. Thus, in one example, with respect to the adjustability of the oscillatory valve, adjusting the angle relationship between the oscillatory valve relative to the nebulizer, airflow mixing channel, and/or mouthpiece can modify an oscillation frequency of the oscillatory valve.

In further detail, in the example shown in FIG. 6, the airflow mixing channel 30 has been modified compared to the airflow mixing channel of FIG. 1. Specifically, the one-way air intake valve 40 in this example is angled downward and attached to angled arm 43 of the airflow mixing channel. This configuration, e.g., angled at from 30° to 90° from perpendicular (perpendicular shown in FIG. 1), can be useful when the one-way valve used operates to some extent based on gravity, e.g., a flapper valve that closes using gravity after user inhalation. Thus, the one-way air intake valve and the one-way medicament 50 valve in this example can be positioned generally in a downward position to allow gravity to close the valves more efficiently when a user is not inhaling.

Figure 9:
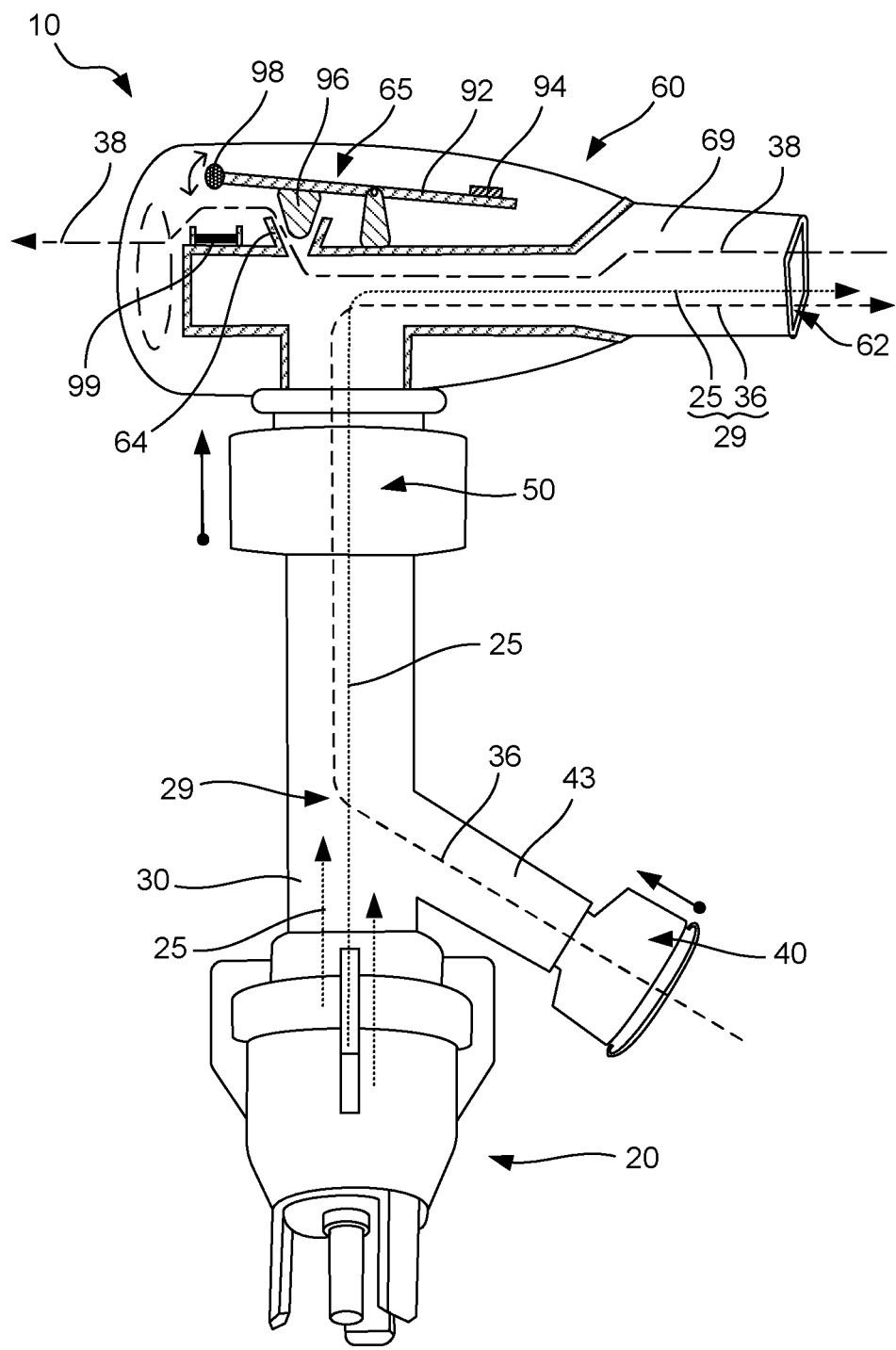
FIG. 9 is a side perspective view of an example respiratory therapy device with partial cross-section of an oscillating positive expiratory pressure assembly in accordance with the present disclosure.

As previously mentioned, any type of oscillatory valve can be used in accordance with examples of the present disclosure. Thus, FIG. 9 represents an alternative respiratory therapy device 10 that can be used in accordance with examples of the present disclosure. In this example, the oscillatory valve 65 also includes an opening defined by a valve seat 64, but rather than a weighted ball, a vibratory "stopper" or plug 96 is associated with an oscillating lever 92. In one example, the oscillating lever can be counter-weighted with a separate or integrated counterweight 94. In another example, the oscillating lever can include a metallic member 98 that may be magnetically associated with a magnet 99 that is magnetically adjacent (on the body of the device) to the metallic member, but not also on the oscillating lever. In one example, the magnetic relationship between the metallic member and the magnet can be adjustable to allow for modulation of the frequency response and/or amplitude of the oscillatory valve. Adjustment can be carried out by a dial, a switch, or by any other mechanical or electromechanical mechanism (not shown) that adjusts the magnetic relationship between the magnet and the metallic member.

Similar to that shown in FIGS. 1-3 and 6, the respiratory therapy device 10 of FIG. 9 can also include a nebulizer 20 (which can be a jet nebulizer, as shown, an ultrasonic wave nebulizer, a vibrating mesh nebulizer, a mechanical nebulizer, etc.) attached to an airflow mixing channel 30. The airflow mixing channel in this example is attached to a one-way air intake valve 40 and a one-way medicament valve 50. The one-way air intake valve is angled generally downward (at from 30° to 90°, and in this example, about 45°) via an angled arm 43 of the airflow mixing channel. The angled arm is positioned at a lower portion of the airflow mixing channel to provide mixing of the aerosolized liquid medicament 25 and air 36 at a location more distal to the one-way medicament valve than shown in other examples. In this configuration, there is more time/distance for mixing to occur during inhalation, as the diluted aerosolized liquid medicament 29 starts to form at a lower portion of the airflow storage channel. Likewise, the one-way medicament valve is also angled down (at 90° in this example, but could be otherwise angled, e.g., from 30° to 90°, for example). In this configuration, gravity closable valves can be used. Notably, gravity closable valves can be used when the valve is horizontal, such as shown in FIGS. 1-3, but when there is some downward angle, more efficient closing may occur. Other types of valves can alternatively be used provided they allow fluid flow in the directions shown in FIG. 3 and provided they substantially prevent backflow of gas or other fluids as described herein.

Thus, in this example, nebulizer 20 generates aerosolized liquid medicament 25 which admixes with inflowing air 36 to form a diluted aerosolized liquid medicament 29. The diluted aerosolized liquid medicament then flows through the one-way medicament valve where the diluted aerosolized liquid medicament is inhaled by the user. Both of the one-way valves associated with the airflow mixing channel do not typically allow the aerosolized liquid medicament to escape the airflow mixing channel except by inhalation by the user, where air is brought in through the one-way air intake valve and the diluted aerosolized liquid medicament flows into an OPEP airflow channel 69. Again, in some instances, the one-way medicament valve may act as a pressure relief valve, but under normal operation, this is typically not the case. Next, upon exhaling by the user, exhaled air 38 is not allowed to return into the airflow mixing channel, but rather is forced through the oscillatory valve as previously described.

FIGS. 10-13 illustrate various oscillating positive expiratory pressure (OPEP) devices that can be fluidly coupled to an airflow mixing channel 30, a nebulizer (not shown), and/or a pivot joint 47, as previously described. However, in these examples, the one-way medicament valve 50 can also be an inhalation oscillatory valve 65A. Thus, during inhalation through a user-interface opening 62, the inhalation oscillatory valve opens and oscillates to generate loosening of respiratory secretions as an exhalation oscillatory valve 65 closes. Then, during exhalation, the inhalation oscillatory valve closes and the exhalation oscillatory valve opens and oscillates to generate loosening and removal of respiratory secretions. Notably, exhalation oscillatory valve 65 has previously been referred to simply as "oscillatory valve 65" but in this example, since there can be two oscillatory valves, the term "exhalation" is used for clarity. Furthermore, though these OPEP assemblies are shown as being associated with the airflow mixing channel and/or pivot joint, these devices can be used simply as positive expiratory pressure devices without an airflow mixing channel, a pivot joint, a nebulizer (not shown, but shown in FIGS. 1-6), etc. Furthermore, in reference to the frequency response and/or other oscillatory valve properties, it is notable that these can vary somewhat based on the user, and whether the oscillatory valve is being used for inhalation or exhalation. Thus, frequency response, for example, can be considered as an average, and when comparing inhalation frequency response to exhalation frequency response, these higher or lower frequency responses can be considered as "relative" to one another.

Figure 10:
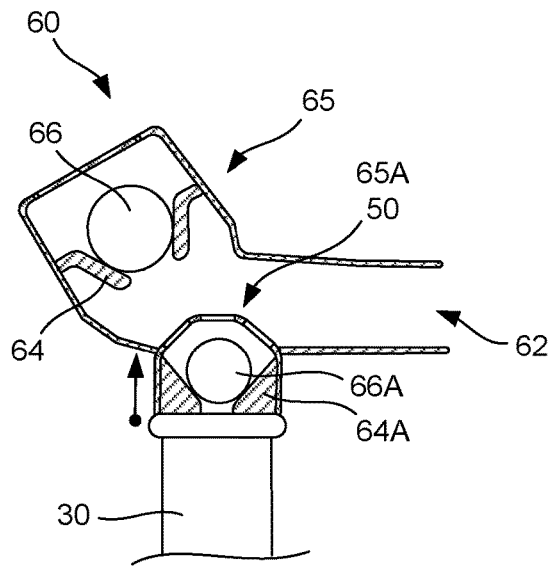
FIG. 10 is a partial cross sectional view of an example oscillating positive expiratory pressure assembly which also includes an oscillatory valve for inhalation, and which can optionally be associated with a nebulizer in accordance with the present disclosure.

In further detail, the oscillating positive expiratory pressure (OPEP) device shown in FIG. 10 can be used as a standalone device with both an inhalation oscillatory valve 65A and an exhalation oscillatory valve 65 providing mechanical vibration suitable for loosening respiratory secretions during both inhalation and exhalation, respectively. By tilting the OPEP assembly similar to that described in FIGS. 7 and 8 (without the use of a pivot joint in this example), the frequency response, amplitude, and/or mean pressure of both inhalation and exhalation can be modified in a coordinated manner. The term "coordinated" in this example includes modification where both the inhalation oscillatory valve and the exhalation oscillatory valve are modified together without independent adjustability. Notably, the respective valve angles for the inhalation oscillatory valve and the exhalation oscillatory valve are different. More specifically, in the example shown, the inhalation oscillatory valve is in more of an upright position, and the exhalation oscillatory valve is in more of a downward angled position. In one example, these angles may be matched (not shown in this FIG. but shown in FIG. 12), or the inhalation oscillatory valve can be at more of a downward angle compared to the exhalation oscillatory valve, potentially demanding greater airflow pressure or force during exhalation than during inhalation. In further detail, with similarly sized valve openings, valve seat configurations, and weighted balls, the inhalation oscillatory valve in the example shown in FIG. 10 may generate a higher frequency response and require a higher mean airflow pressure to actuate the oscillatory valve. However, in this example, the weighted ball of the inhalation oscillatory valve is smaller, which may represent a lighter weighted ball (if the weighted balls are of the same density or material). Thus, different densities or ball sizes as well as different valve seat sizes and angular configurations can be used to adjust the respective oscillatory valve parameters to generate different (or the same if desired) frequencies, amplitudes, mean pressures, etc. Though, as mentioned, this device can be used as a standalone device, it is also notable that the OPEP assembly shown in FIG. 10 can be fluidly associated with a nebulizer (not shown), an airflow mixing channel 30, and a one-way air intake valve (not shown), and can operate similarly to respiratory therapy devices shown and described in FIGS. 1-3, with the added benefit that the one-way medicament valve 50 (or 65A) also provides oscillating inhalation therapy.

Figure 11:
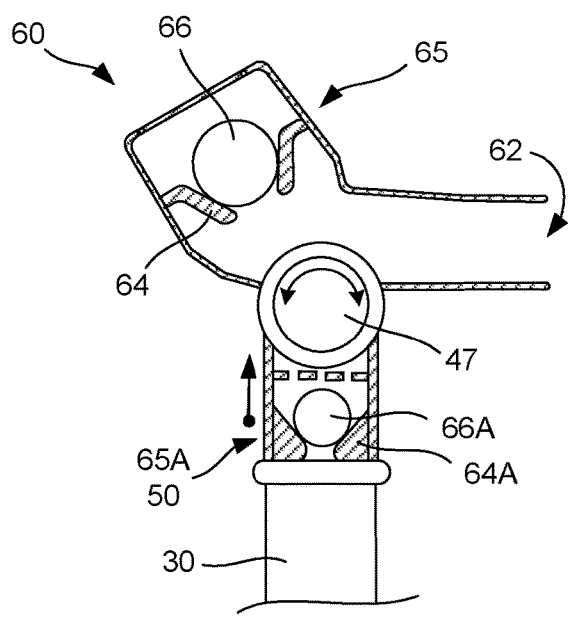
FIG. 11 is a partial cross sectional view of an example oscillating positive expiratory pressure assembly which also includes an oscillatory valve for inhalation and a fluid-directing pivot joint therebetween for modulating a frequency response of an exhalation oscillatory valve relative to an inhalation oscillatory valve, and which can optionally be associated with a nebulizer in accordance with the present disclosure.

The oscillating positive expiratory pressure (OPEP) device shown in FIG. 11 can also be used as a standalone device with both an inhalation oscillatory valve 65A and an exhalation oscillatory valve 65 providing mechanical vibration suitable for loosening respiratory secretions during both inhalation and exhalation, respectively. However, unlike the OPEP assembly in FIG. 10, this OPEP assembly includes a pivot joint 47 positioned between the inhalation oscillatory valve and an exhalation oscillatory valve. The pivot joint obscures the fluid channel, but it is noted that oscillatory valves are both fluidly coupled to a mouthpiece and to one another (opening and closing as appropriate). With the pivot joint positioned between the two oscillatory valves, the inhalation oscillatory valve and an exhalation oscillatory valve can be oppositionally tiltedtitled (angular movement in opposite directions). Thus, rather than a coordinated or unified valve adjustment (in the same angular direction) as with FIG. 10, independent or oppositional tilting of the two oscillatory valves can provide a user the ability to adjust inhalation parameters (frequency response, amplitude, and/or pressure) to a first set of values, and in the opposite angular direction, adjust the exhalation parameters to a second set of values. For example, a user may elect to increase the frequency response, amplitude, and/or mean pressure during exhalation by tilting or angling the exhalation oscillatory valve upward (to a valve angle similar to that shown in FIG. 8), while at the same time elect to decrease the frequency response, amplitude, and/or mean pressure during inhalation by tilting or angling the inhalation oscillatory valve downward (to a valve angle similar to that shown in FIG. 7). This may provide a therapy setting where more force is used to exhale, contributing to removing respiratory secretions, and less force is used to inhale to more gently loosen secretions without significant risk of inhaling dislodged secretions deeper into the lung tissue. In another example, this relationship where the inhalation oscillatory valve is set to require a lower mean airflow pressure than the exhalation oscillatory valve does not require a pivot joint or other relative angle adjustment mechanism. This relationship can be fixed, similar to that shown in FIG. 10, except that the angles of the respective oscillatory valves are reversed, i.e. more downward angle for the inhalation oscillatory valve and more upward angle for the exhalation oscillatory valve. In further detail, as mentioned, the OPEP assembly shown in FIG. 11 can be used as a standalone device without the airflow mixing channel 30 and other components previously described, e.g., nebulizer, one-way inhalation valve, etc. However, in one example, the OPEP assembly can be fluidly associated with a nebulizer (not shown), the airflow mixing channel 30, and a one-way air intake valve (not shown), and can operate similarly to respiratory therapy devices shown and described in FIGS. 1-8, with the added benefit that the one-way medicament valve 50 (or 65A) also provides oscillating inhalation therapy.

Figure 12:
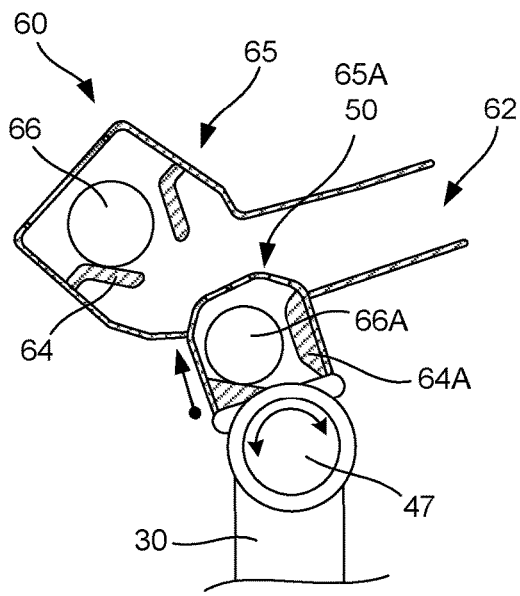
FIG. 12 is a partial cross sectional view of an example oscillating positive expiratory pressure assembly which also includes an oscillatory valve for inhalation and a fluid-directing pivot joint modulating a frequency response of an exhalation oscillatory valve and an inhalation oscillator valve relative to an airflow mixing channel (and/or nebulizer) in accordance with the present disclosure.

In another example, the oscillating positive expiratory pressure (OPEP) device shown in FIG. 12 is similar to that shown in FIG. 10, except that the OPEP assembly includes a pivot joint 47 which provides a mechanism for pivoting the OPEP assembly as a whole relative to the airflow mixing channel 30 and/or the nebulizer (not shown, but shown in FIGS. 1-6). Thus, the example shown in FIG. 12 is similar to the examples shown in FIGS. 6-8, except that the one-way medicament valve 50 in this example is an inhalation oscillatory valve 65A. Furthermore, in this example, notably the inhalation oscillatory valve and the exhalation oscillatory valve are shown as similarly configured with the same relative angles and opening sizes for the valve seat and the weighted ball. Thus, when the OPEP assembly (with one-way medicament valve) is tilted, the relative parameters are fixed provided the valves can be adjusted in a coordinated manner (in the same angular direction) to similar settings. Again, these fixed relative valve angles are the same in the example, but can be different as shown in FIG. 10, or in an opposite configuration as shown in FIG. 10 (inhalation oscillatory valve being at a more downward angle relative to the exhalation oscillatory valve).

Figure 13:
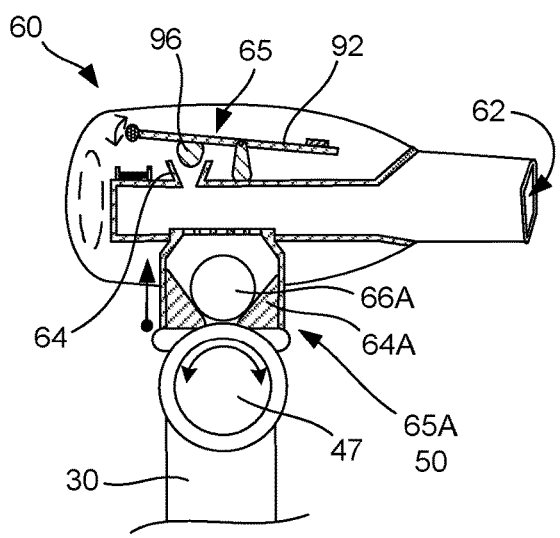
FIG. 13 is a partial cross sectional view of an example oscillating positive expiratory pressure assembly which also includes an oscillatory valve for inhalation, and which can optionally be associated with a nebulizer in accordance with the present disclosure.

In another example, the oscillating positive expiratory pressure (OPEP) device shown in FIG. 13 utilizes two different types of oscillatory valves. In this example, the inhalation oscillatory valve 65A includes a weighted ball and a valve seat, similar to that shown in FIGS. 1-3, 7, 8, and 10-13. The exhalation oscillatory valve 65 can be similar to that shown in FIG. 9, which utilizes an oscillating lever, a stopper (analogous to the weighted ball), and a valve seat to generate the oscillatory therapy effect. Again, this device can be used as a standalone device with both the inhalation oscillatory valve and the exhalation oscillatory valve providing mechanical vibration suitable for loosening respiratory secretions during both inhalation and exhalation, respectively. As a standalone device, the pivot joint may not be needed. Furthermore, with this particular arrangement, the exhalation vibratory valve may not be particularly impacted by the effects of gravity so a pivot joint positioned between the two oscillatory valves may also not be present, but could be included to provide user comfort, for example, e.g., user adjusts the angle of the inhalation oscillatory valve relative to a comfortable position of the exhalation oscillatory valve. Whether a pivot joint is used or not, by tilting or angling the inhalation oscillatory valve upward, increased frequency response, amplitude, and/or mean pressure can be realized, and at the same time, the exhalation oscillatory valve may remain essentially unaffected. The exhalation oscillatory valve can alternatively be adjusted mechanically as described previously in FIG. 9. Though the OPEP assembly shown in FIG. 13 can be used as a standalone device without the airflow mixing channel 30 and other components previously described, e.g., nebulizer, one-way inhalation valve, etc., in one example, the OPEP assembly can be fluidly associated with a nebulizer (not shown), the airflow mixing channel 30, and a one-way air intake valve (not shown). The pivot joint can be positioned to adjust the inhalation oscillatory valve relative to the airflow mixing channel and/or nebulizer, and can operate similarly to respiratory therapy devices shown and described in FIG. 9, and/or pivot similarly to that shown in FIGS. 6-8, with the added benefit that the one-way medicament valve 50 (or 65A) also provides oscillating inhalation therapy.

There can be other oscillating PEP assemblies that can be used in connection with the present respiratory therapy devices of the present disclosure. For example, the Aerobika® Oscillating Positive Expiratory Pressure Therapy System (from Monaghan) can be modified to be used with the other components of the respiratory therapy devices shown in FIGS. 1-9. With the Aerobika® device, exhaled gas passes through a one-way valve housed within a chamber, creating airflow oscillations and positive expiratory pressure as the valve chatters. The oscillatory valve in this system, thus, can function similarly to the oscillatory valves shown and described herein. Furthermore, the Aerobika® device can include a dial that adjusts the resistance setting and/or the ease with which the one-way valve opens and closes. Modification to allow for diluted aerosolized liquid medicament to enter and be inhaled by the user can occur by opening a side wall for attachment to the one-way medicament valve, for example. Another oscillating PEP assembly that can be modified and used in accordance with the present respiratory therapy devices is the RC-Cornet® (from R. Cegla GmbH & Co.). With this device, exhaled gas passes through a curved plastic tube containing a flexible hose and sound damper. The hose, essentially, erratically strikes the top and bottom of the curved plastic tube, intermittently occluding flow and creating oscillation or a vibratory effect. The device can be adjusted by changing the size of the expiratory resistor, which adjusts the frequency response, amplitude, and/or mean pressure. Again, modification can occur by creating an opening that can be coupled to the one-way medicament valve for inhalation of diluted aerosolized liquid medicament therethrough. The Flutter® Mucous Clearance Device (from VarioRaw Percutive S.àr.I.) operates similarly to that shown at 60 in FIGS. 1-3, but does not include an opening used to receive aerosolized liquid medicament from a one-way medicament valve. Thus, the Flutter® can be modified accordingly to be used in accordance with examples of the present disclosure. Another type of positive expiratory pressure device is sold commercially as the Acapella® Vibratory PEP Therapy System (from Smiths Medical). The Acapella® system can operate similarly to that shown in FIG. 9 and can be modified to include an opening for receiving aerosolized liquid medicament suitable for the respiratory therapy systems disclosed herein. Furthermore, any other oscillating PEP assembly that can be modified to receive aerosolized liquid medicament during inhalation and which can still remain suitable for oscillating positive expiratory pressure therapy during exhalation can be used in accordance with examples of the present disclosure.

Thus, in examples where an oscillating positive expiratory pressure assembly includes both an inhalation oscillatory valve and an exhalation oscillatory valve, many of the same details described with respect to OPEP devices can be used for either valve. Some valves may benefit from modifying the airflow for inhalation so that inhalation actuates the oscillatory valve rather than exhalation, as would be appreciated by one skilled in the art after considering the present disclosure.

In still further detail, in accordance with the examples shown and described in FIGS. 10-13, as mentioned, there can be two types of devices that include multiple oscillatory valves, namely an oscillating positive expiratory pressure assembly or a respiratory therapy device. The oscillating positive expiratory pressure assembly can include an inhalation oscillatory valve 65A and an exhalation oscillatory valve 65. The assemblies can further include a user-interface opening 62 in fluid communication with the inhalation oscillatory valve and the exhalation oscillatory valve, such that upon inhalation by a user the inhalation oscillatory valve provides a first frequency response and the exhalation oscillatory valve is closed, and upon exhalation by the user the exhalation oscillatory valve provides a second frequency response and the inhalation oscillatory valve is closed.

The respiratory therapy device, on the other hand, can include a nebulizer (not shown, but shown in FIGS. 1-6 and 9), an inhalation oscillatory valve 65A fluidly coupled to and configured to receive aerosolized liquid medicament from the nebulizer, and an exhalation oscillatory valve 65. A user-interface opening 62 can be in fluid communication with the inhalation oscillatory valve and the aerosolized liquid medicament during inhalation, and in fluid communication with the exhalation oscillatory valve during exhalation. Thus, the inhalation oscillatory valve can generate a first frequency response and the exhalation oscillatory valve can generate a second frequency response.

In further detail, the inhalation oscillatory valve 65A and the exhalation oscillatory valve 65 as shown and described with respect to FIGS. 10-13 may include various features and functionalities that can be implemented. For example, the first frequency response and the second frequency response generated by the two oscillatory valves can be about the same, or the first frequency response can be higher than the second frequency response, or the first frequency response can be lower than the second frequency response. In further detail, a single adjustment (such as tilting the oscillating PEP assembly either with or without the use of a pivot joint 47) can provide a coordinate adjustment of both the first frequency response and the second frequency response, e.g., the frequency can be increased essentially uniformly for both the inhalation oscillatory valve and the exhalation oscillatory valve. In another example, a single adjustment (such as adjusting a pivot joint between the two oscillatory valves) can increase the first frequency response and decrease the second frequency response. In still another example, a single adjustment (such as adjusting a pivot joint between the two oscillatory valves) can decrease the first frequency response and increase the second frequency response.

The inhalation oscillatory valve 65A and the exhalation oscillatory valve 65 can each include a weighted ball 66,66A and a valve seat 64,64A for receiving the weighted ball and allowing inhaled or exhaled air, respectively, to oscillate the weighted ball over or adjacent to the valve seat. Thus, the OPEP assembly or the respiratory therapy device can include a pivot joint 47 that can be positioned between the inhalation oscillatory valve and the exhalation oscillatory valve. In another example, the weighted ball 66A of the inhalation oscillatory valve 65 and the weighted ball 66 of the exhalation oscillatory valve 65 can be different in size, density, weight, or a combination thereof. In still another example, the weighted ball 66A of the inhalation oscillatory valve 65 and the weighted ball 66 of the exhalation oscillatory valve 65 can each generate a different frequency response even if the respective oscillatory valves are at the same relative angle. In further detail, the inhalation oscillatory valve and the exhalation oscillatory valve can be selected from two different oscillating mechanisms. For example, as shown specifically in FIG. 13, the inhalation oscillatory valve 65A can include a valve seat 64A and a weighted ball 66A, and the exhalation oscillatory valve 65 can include an oscillating lever 92 associated with a stopper 96 and a valve seat 64. In one specific example, a pivot joint 47 can be positioned between the inhalation oscillatory valve and the exhalation oscillatory valve. Thus, regardless of the example (with or without a nebulizer, type of oscillatory valve, properties of the oscillatory valve components, etc.), there can be a pivot joint positioned between the inhalation oscillatory valve and the exhalation oscillatory valve to adjust the angular relationship between the two valves. In other examples, there may not be a pivot joint positioned between the inhalation oscillatory valve and the exhalation oscillatory valve. In still other examples, particularly when fluidly associated with the nebulizer, the pivot joint can be operationally positioned to modify the angular relationship between the inhalation oscillatory valve and the airflow mixing channel 30 and/or the nebulizer. In other examples, the first frequency response and the second frequency response can be modified by adjusting an operational angle of the inhalation oscillatory valve and the exhalation oscillatory valve in a coordinated manner, e.g., angle adjusted together by tilting both valves by the same angle, relative to a neutral or standard position, e.g., relative to a generally horizontal mouthpiece. Alternatively, the first frequency response and the second frequency response can be oppositionally modifiable by adjusting an operational angle of the inhalation oscillatory valve relative to the exhalation oscillatory valve. In another example, the first frequency response and the second frequency response can be independently modifiable by different mechanical mechanisms, such as by any two of: adjusting an angle or tilt, mechanically adjusting a counterweighted lever, spatially adjusting a relationship between a magnet and a metal portion of an oscillating lever, adjusting a valve opening size, or adjusting a chattering valve.

With more specific reference to the respiratory therapy devices of the present disclosure which include both an inhalation oscillatory valve 65A and an exhalation oscillatory valve 65, in one example, an airflow mixing channel 30 can be positioned between and in fluid communication with the nebulizer and the inhalation oscillatory valve. For example, the airflow mixing channel can include a first inflow opening in fluid communication with the nebulizer, a second inflow opening, and an outflow opening in fluid communication with the inhalation oscillatory valve. These components can be seen in greater detail in FIGS. 1-3, 6, and 9. The second inflow opening can include a one-way air intake valve in fluid communication therewith. Thus, in examples where the airflow mixing channel is positioned between and in fluid communication with the nebulizer and the inhalation oscillatory valve, the one-way air intake valve can be the inhalation oscillatory valve (not shown), and thus examples herein include such embodiments. In such examples, the one-way medicament valve may not be present, or may be present, such as in the form of a rubber stopper valve. In this configuration, the vibratory or oscillatory effect can be introduced to the user during inhalation such that the aerosolized medicament does not pass through the inhalation oscillatory valve, rather the inhalation oscillatory valve merely introduces air from outside of the airflow mixing channel to mix with the aerosolized liquid medicament as a diluent.

Figure 14:
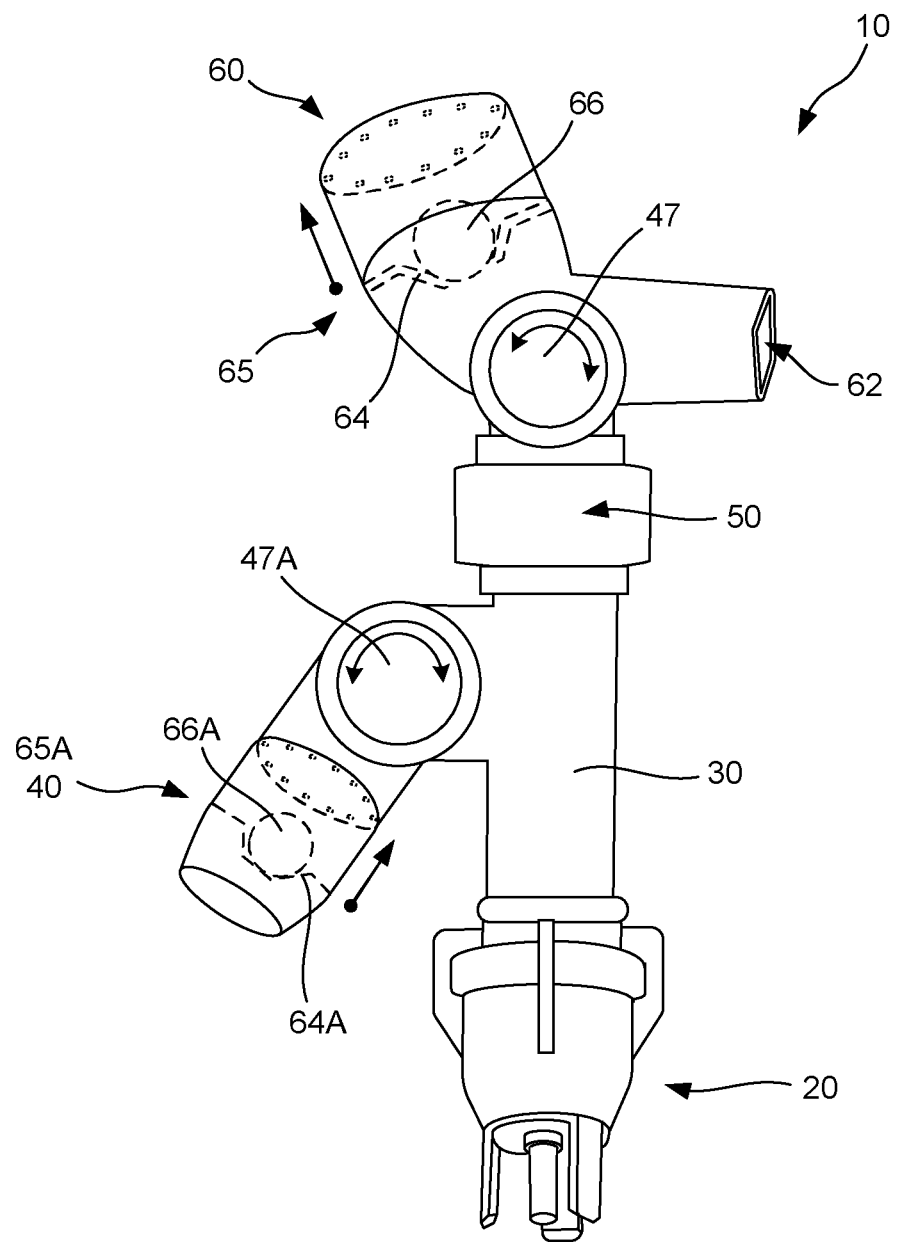
FIG. 14 is a side perspective view of an example respiratory therapy device similar to that shown in FIG. 6, but which also includes an example tiltable inhalation oscillatory valve acting as the one-way air intake valve in accordance with the present disclosure.

FIG. 14 illustrates an embodiment of a respiratory therapy device 10 where an inhalation oscillatory valve 65A is also the one-way air intake valve 40, with a weighted ball 66A associated with a valve seat 64A. In this example, the inhalation oscillatory valve can be fluidly coupled to an airflow mixing channel 30, and can be independently tiltable with respect to the airflow mixing channel and/or the nebulizer 20 using a pivot joint 47A. Also, as shown in this example, the respiratory therapy device can be adapted so that the angular relationship between the exhalation oscillatory valve 65 and the airflow mixing channel or nebulizer can also be modified using a pivot joint 47. The exhalation oscillatory valve in this example can also include a weighted ball 66 and a valve seat 65, for example. Notably, any other type of oscillatory valve can be used instead of the weighted ball and valve seat systems shown generally at 65 or 65A. With some types of oscillatory valves, a pivot joint may or may not be present for adjustability. However, with this example, both oscillatory valves can be independently pivotable or tiltable with respect to the airflow mixing channel. In further detail, the pivot joints shown at these example locations could alternatively be positioned elsewhere on the respiratory therapy device, such as between the nebulizer and the airflow mixing channel, or between the user-interface opening 62 and the exhalation oscillatory valve, for example. Essentially, the pivot joint can be anywhere on the device where an angular relationship between either of the oscillatory valves or any other structure may be desirable so that the valve can be angularly adjusted while allowing the other features of the respiratory therapy device to function properly, desirably, and/or ergonomically.

Relative adjustment of the inhalation oscillatory valve 65A compared to the exhalation oscillatory valve 65 can be set for providing any of a number of therapeutic effects. For example, the user-interface opening 62 can be in fluid communication with the inhalation oscillatory valve and aerosolized liquid medicament during inhalation, with oscillating airflow being received from the inhalation oscillatory valve and aerosolized medicament being received from the nebulizer 20 for mixing in the airflow mixing channel 30. The user-interface opening can also be in fluid communication with the exhalation oscillatory valve during exhalation. Thus, the inhalation oscillatory valve can generate a first frequency response and the exhalation oscillatory valve can generate a second frequency response. Typically, while the inhalation oscillatory valve is open, the exhalation oscillatory valve can be closed, and vice versa. In further detail, the inhalation oscillatory valve and the exhalation oscillatory valve can be set to include various frequency responses, amplitudes, mean airflow pressures, etc. For example, a first frequency response (or other airflow parameter) generated by the inhalation oscillatory valve and the second frequency response (or other airflow parameter) generated by the exhalation oscillatory valve can be about the same, or the first frequency response can be higher than the second frequency response, or the first frequency response can be lower than the second frequency response. Additional detail regarding the variability of the frequency response, amplitude, mean airflow pressure, etc., is described with respect to FIGS. 10-13, and the same can be applicable to the present example, even when the inhalation oscillatory valve is being used as the one-way air intake valve 40 rather than the one-way medicament valve 50.

With respect to FIGS. 10-14, other features similar to those described with respect to FIGS. 1-9 can also be present, such as the utilization of various types of nebulizers, the efficiency of delivered aerosolized liquid medicament, e.g., at least 60 vol %, at least 75 vol %, or the like, and those various advantages can be applicable to these examples as well.

FIG. 15 depicts an alternative respiratory therapy system, in the form of respiratory therapy assembly kits. For example, many different interchangeable parts that may be present in an example respiratory therapy assembly kit are shown so that a user may assemble, acquire and use only the specific parts that the user desires to assemble and use, or so that the user may purchase a variety of parts and assemble the respiratory therapy assembly kit for a specific therapy. Thus, a user, or a medical professional, can put together the device that would be useful for a particular therapy. The interchangeable parts shown in FIG. 15 can, in some instances, function in alignment with the sub-structures shown and described in FIGS. 1-14, and thus, those descriptions are incorporated to the respiratory therapy assembly kit(s) such as those described by way of example in FIG. 15. For example, part (i) can be considered in some examples as analogous to the oscillating positive expiratory pressure assemblies 60 shown in FIGS. 1-3, 6-8, 10-12, and 14; part (ii) can be considered in some examples as analogous to the oscillating positive expiratory pressure assemblies 60 shown in FIGS. 9 and 13; part (iii) is not an oscillating positive expiratory pressure assembly but can be used when oscillatory exhalation therapy is not being used; parts (iv), (v), and (vi) can be considered in some examples as analogous to the various one-way valves 40, 50, 65A of FIGS. 1-3 and 6-14 and depending on their location of use, can be a one-way air intake valve 40, 65A or a one-way medicament valve 50, 65A; part (vii) can be considered in some examples as analogous to the pivot joints 47 shown in FIGS. 6-8 and 11-14; part (viii) can be considered in some examples as analogous to the airflow mixing channels 30 shown in FIGS. 1-3 and 6-14; and part (ix) can be considered in some examples as analogous to the nebulizers 20 shown in FIGS. 1-5, 6-9, and 14.

In more specific detail regarding FIG. 15, an example respiratory therapy assembly kit 100 is shown that includes multiple interchangeable parts. As a note, a kit need not include every one of the parts shown in FIG. 15, as there can be kits including three of the parts shown, kits including four of the parts shown, kits including five of the parts shown, kits including six of the parts shown, kits including seven of the parts shown, kits including eight of the parts shown, and so forth. Additionally, there can be kits that include parts that are not shown, such as other types of fittings or connectors, multiple types of fittings to connect to different types of nebulizers, tubes, other airflow directing channeling devices, etc. Also, in one example, the kit does not include the nebulizer, shown at (ix), as that may be a device already possessed by the user, and the respiratory therapy assembly kit may rather be adapted to connect to a nebulizer that the user already possesses.

By way of specific example, as shown in FIG. 15, there can one or multiple types of mouthpiece(s), e.g., (i), (ii), and/or (iii); one-way valve(s), e.g., (iv), (v), and/or (vi); a pivot joint(s) (vii); and/or airflow mixing channel(s) (viii). Also shown in this example is a nebulizer (ix), which can be fluidly coupled to one or more structure(s) of this or another respiratory therapy assembly kit 100. Mouthpieces (i) and (ii) in this example are both oscillating positive expiratory pressure assemblies (of different types) with the exhalation opening fluidly associated with an exhalation oscillatory valve.

Mouthpiece (i) of FIG. 15 includes an inhalation opening 61, a user-interface opening 62, and an exhalation opening 63. The inhalation opening in this example can include a cage 67A or some other structure, e.g., narrowed opening, screen, cross-bar, etc., that may be usable when used with an (inhalation) oscillatory valve (iv) with a weighted ball 66A, for example. A cage or other constricting structure can be used to prevent inhalation of the weighted ball through the user-interface opening. An (exhalation) oscillatory valve 65 is also shown, where exhaled air causes a weighted ball 66 to vibrate or oscillate over an opening of a valve seat 64 where the exhaled air can escape through a series of perforations 68 in its valve cap 67. Furthermore, because of the presence of the one-way medicament valve, the exhaled air is not allowed to re-enter or flow back into the airflow mixing channel, and thus, essentially the entire exhalation of the user is directed toward the oscillatory valve, which provides for a more efficient use of the oscillatory valve and general OPEP therapy. In one example, there can also be a plurality of weighted balls of different weights to provide different levels of oscillatory resistance when actuated by exhalation.

Mouthpiece (ii) of FIG. 15 is a different type of oscillatory valve 65 which also includes an inhalation opening 61, a user-interface opening 62, and an exhalation opening 63.

The inhalation opening and the user-interface opening can be as described with respect to mouthpiece (i), for example. In this example, the exhalation opening can be defined by a valve seat 64, but rather than a weighted ball, a vibratory "stopper" or plug 96 is associated with an oscillating lever 92. In one example, the oscillating lever can be counter-weighted with a separate or integrated counterweight (see FIG. 9). In another example, the oscillating lever can include a metallic member that may be magnetically associated with a magnet that is magnetically adjacent (on body of the device) to the metallic member, but not also on the oscillating lever (see FIG. 9). A cage 67A is shown in this example, but may not be needed as long as the weighted ball does not have access to leave its general area for use with its one-way valve, for example.

Figure 15:
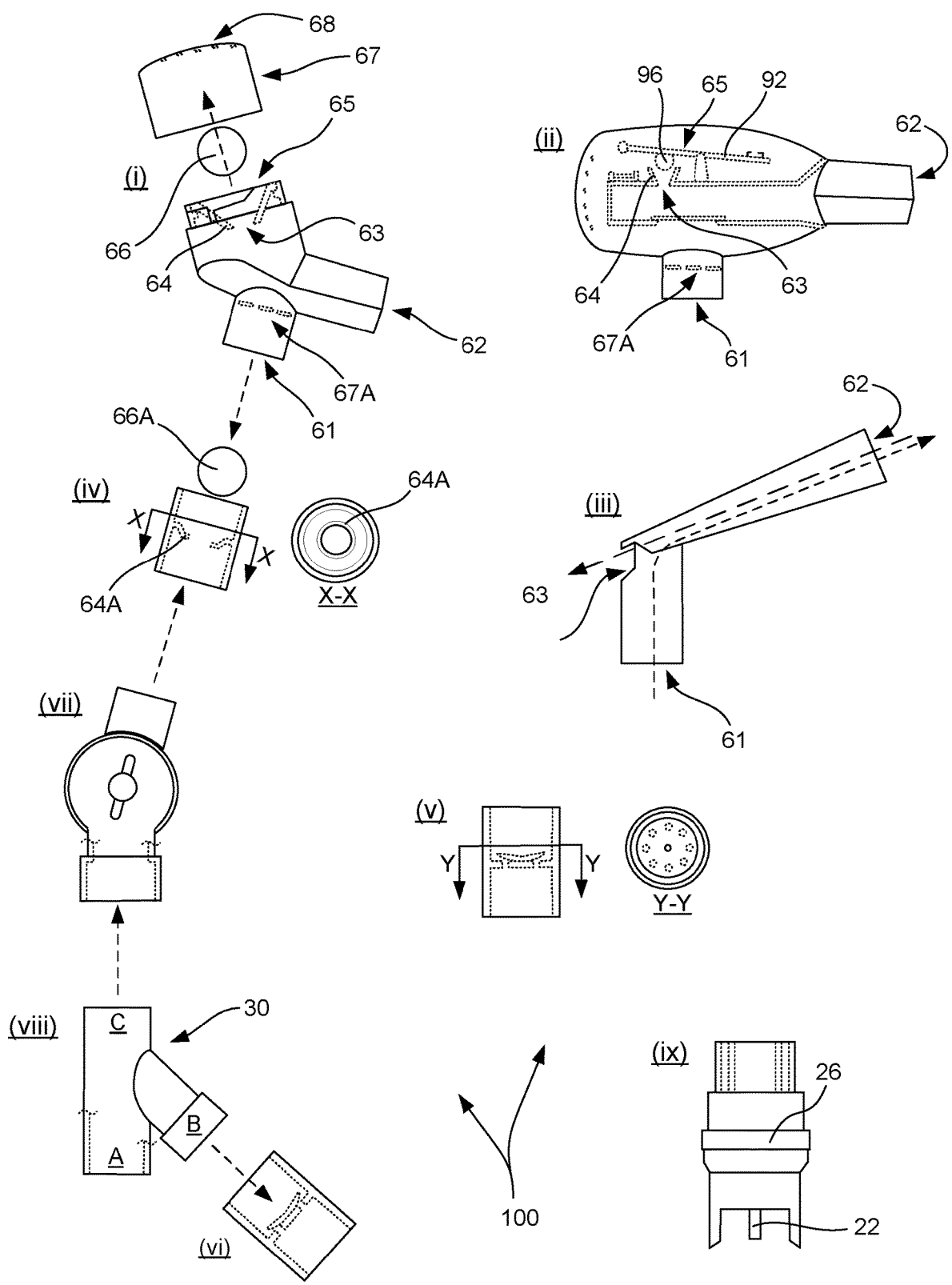
FIG. 15 is a side view of an example respiratory therapy system or kit with interchangeable parts in accordance with the present disclosure.

Mouthpiece (iii) of FIG. 15 is an example airflow mouthpiece that is not an oscillatory mouthpiece, but rather a mouthpiece often used with nebulizers. This mouthpiece also includes an inhalation opening 61, a user-interface opening 62, and an exhalation opening 63. If a user does not want to use an (exhalation) oscillatory valve, this mouthpiece can be swapped out for use, for example. In this example, the throat of the airflow channel is narrow enough that a weighted ball (if used) would be too narrow to escape the inhalation opening channel during inhalation, so a cage is not present, but other arrangements utilize a cage, depending on the size relationships between the weighted ball and channels for airflow.

As mentioned, FIG. 15 also provides a plurality of one-way valves (iv), (v), (vi), one of which in the kit shown is an (inhalation) oscillatory valve, shown at (iv). The other two one-way valves are shown at (v) and at (vi). These two types of valves are the same valve type, but one is shown as being usable as a one-way air intake valve 40 and the other is shown as being usable as a one-way medicament valve. Any of these valves can be interchangeable with any of the other valves in this kit. For example, there can be one inhalation oscillatory valve used and one non-oscillatory one-way valve used, or if there is not intent on inhalation oscillatory therapy, both valves can be non-oscillatory valves. In other examples, it may be that only a single one-way valve is elected for use (of either type at either location). The oscillatory one-way valve shown at (iv) includes a weighted ball (or multiple weighted balls of different size, weight, etc.), and a valve seat 64A. During inhalation, the weighted ball can provide an oscillatory effect to the user. Also, this particular ball valve can provide a good seal to prevent leakage of aerosolized medicine back into any chamber that may be connected there-beneath. Section X-X of structure (iv) shows a cross-sectional top view of the valve seat, with the very central-most circle depicting an opening of the valve seat where airflow and aerosolized medicament can flow during oscillatory inhalation by a user, for example. One-way valves shown (v) and (vi) in cross-section along section Y-Y, include a flexible membrane that opens and closes airflow openings during inhalation and exhalation, respectively. This type of valve is not an oscillatory valve, but does provide for one-way airflow during use.

Regarding the airflow mixing channel shown at (viii) (and shown and described in some detail with respect to FIGS. 1 and 2), there are multiple openings associated therewith, namely a first inflow opening "A," a second inflow opening "B," and an outflow opening "C." The first inflow opening can be couplable with a nebulizer, such as the nebulizer shown at (ix). Typically, the nebulizer can include a gas intake interface 22 and a nebulizer cup 26, for example. The plurality of one-way valves shown at (iv), (v), and (vi) can be interchangeably fluidly couplable to the airflow mixing channel, either directly or through another intervening fluid-directing structure, such as the fluid directing pivot joint shown at (vii). In one example, the plurality of one-way valves can be interchangeably fluidly couplable to the inhalation opening of the mouthpiece through the fluid-directing pivot joint. In further detail, the plurality of one-way valves can be interchangeably fluidly couplable to the outflow opening of the airflow mixing channel through the fluid-directing pivot joint.

In further detail regarding the airflow mixing channel shown at (viii), one of the one-way valves can be fluidly coupleable to the outflow opening "C" so that it operates as a one-way medicament valve, and another of the one-way valves can be fluidly coupleable to the second inflow opening "B" it operates as a one-way air intake valve. As mentioned, in one example, the respiratory therapy assembly kit can include at least two one-way valves, or at least three one-way valves that are independently interchangeable. The one-way valves can be interchangeable to be both fluidly couplable to provide one-way airflow from the outflow opening of the airflow mixing channel to the inhalation opening 61 of the mouthpiece, and fluidly couplable to the second inflow opening.

The various parts of the respiratory therapy assembly kit shown in FIG. 16 can have the following internal volumes, for example. The oscillating positive expiratory pressure assembly shown at (i) (excluding the volume of the cap 67 and the volume displaced by the weighted ball 66) can be from about 20 cc to about 50 cc, from about 25 cc to about 45 cc, or from about 30 cc to about 35 cc, by example only and without limitation. The oscillating positive expiratory pressure assembly shown at (ii) can be from about 25 cc to about 100 cc, from about 30 cc to about 80 cc, or from about 40 cc to about 70 cc, by example only and without limitation. The airflow mouthpiece shown at (iii), for example can be from about 10 cc to about 50 cc, from about 15 cc to about 45 cc, or from about 20 cc to about 40 cc, by example only and without limitation. The one-way valves shown at (iv), (v), and (vi) (excluding the volume of the weighted ball) can be from about 5 cc to about 25 cc, from about 7 cc to about 20 cc, or from about 10 cc to about 15 cc, by example only and without limitation. The fluid-directing pivot joint shown at (vii) can have an internal volume from about 20 cc to about 60 cc, from about 25 cc to about 50 cc, or from about 30 cc to about 40 cc, by example only and without limitation. The airflow mixing channel shown at (viii) can have an internal volume from about 15 cc to about 50 cc, from about 20 cc to about 40 cc, from about 22 cc to about 30 cc, or from about 15 cc to about 25 cc, by example only and without limitation. Other volumes can likewise be used, and it is noted that when these parts are assembled into a functioning respiratory therapy device, due to overlap where the parts may be assembled or fitted together, the total internal volume may be reduced slightly due to redundant volumes where two parts are joined together in some examples.

Turning now to FIG. 16, the present disclosure is also drawn to a method 200 of treating a respiratory disease or condition include delivering 210 an aerosolized liquid medicament to an airflow mixing channel prior to inhalation by a user; flowing 220 air through a one-way air intake valve into the airflow mixing channel to mix with the aerosolized liquid medicament and form a diluted aerosolized liquid medicament; and flowing 230 the diluted aerosolized liquid medicament through a one-way medicament valve and into lung airways of the user. An additional step can include flowing 240 exhaled air from the user through an oscillatory valve. In one example, the method can further include a preliminary step of generating the aerosolized liquid medicament, typically from a liquid medicament reservoir. In one specific example, either the one-way air intake valve or the one-way medicament valve can be an inhalation oscillatory valve to provide oscillatory treatment during inhalation. The other one-way valve can be a more standard one-way valve, such as a one-way rubber stopper valve.

Figure 17:
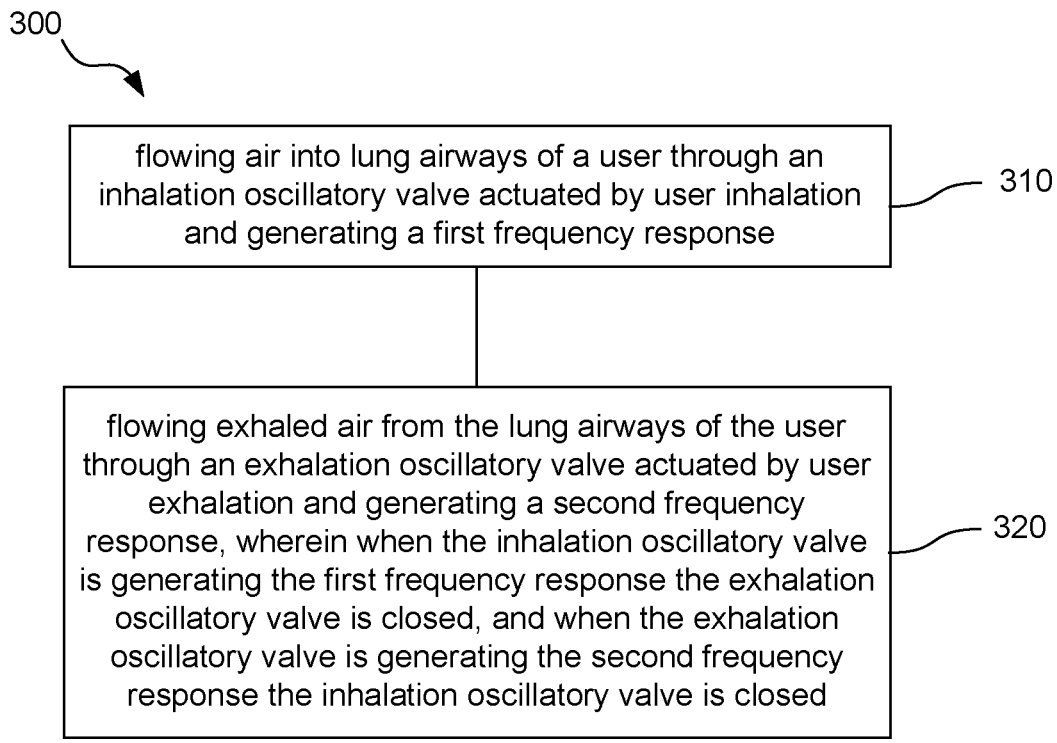
FIG. 17 is a flow diagram that graphically depicts an example method of treating a respiratory disease or condition in accordance with the present disclosure.

FIG. 17 also illustrates a method 300 of treating a respiratory disease or condition, which can include flowing 310 air into the lung airways of a user through an inhalation oscillatory valve actuated by user inhalation and generating a first frequency response, and flowing 320 exhaled air from the lung airways of the user through an exhalation oscillatory valve actuated by user exhalation and generating a second frequency response. When the inhalation oscillatory valve is generating the first frequency response, the exhalation oscillatory valve is closed, and when the exhalation oscillatory valve is generating the second frequency response, the inhalation oscillatory valve is closed.

Figure 18:
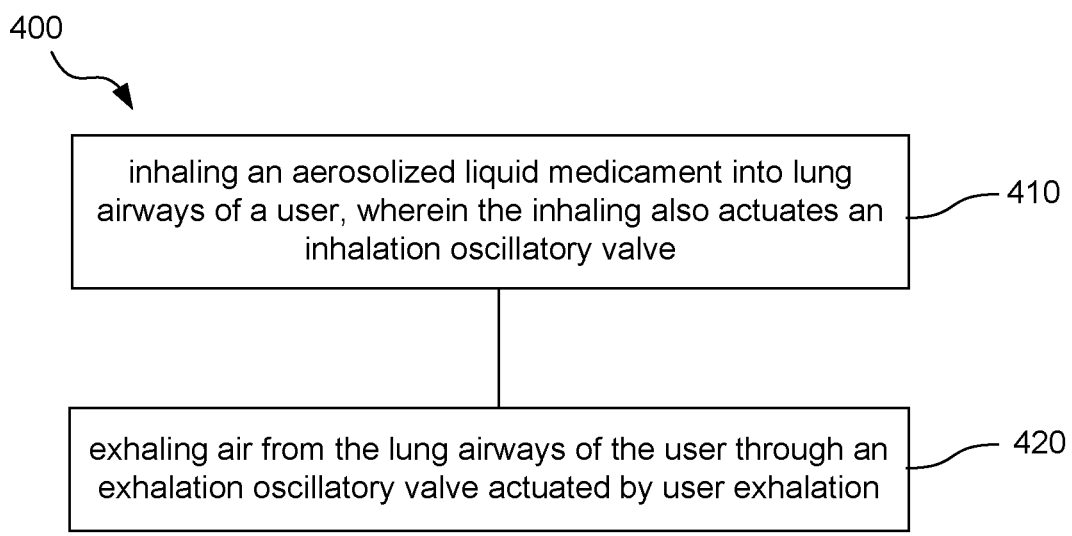
FIG. 18 is a flow diagram that graphically depicts an example method of treating a respiratory disease or condition in accordance with the present disclosure.

In another example, FIG. 18 depicts a flow chart of a method 400 of treating a respiratory disease or condition, which can include inhaling 410 an aerosolized liquid medicament into lung airways of a user, wherein the inhaling also actuates an inhalation oscillatory valve. The method can also include exhaling 420 air from the lung airways of the user through an exhalation oscillatory valve actuated by the exhalation. In certain examples, these oscillatory valves generate a frequency response to the respiratory system of the user, and the frequency response during inhalation and exhalation can be the same or different, depending on valve configurations as described in detail elsewhere herein.

In each of these methods, each includes the use of an (exhalation) oscillatory valve for exhalation, but the latter two examples shown in FIGS. 17 and 18 may also include the use of an inhalation oscillatory valve. Furthermore, FIGS. 17 and 18 both may include steps of flowing or inhaling aerosolized liquid medicament (either diluted or not) into lung airways of a user. Thus, there are certain common features within these three example methods, and certain features that can be different from method to method.

Thus, in certain methods of treating a respiratory disease or condition of the present disclosure, some examples can further include a preliminary step of generating the aerosolized liquid medicament in a nebulizer, such as by the use of a pressurized gas jetted through a liquid medicament, by the use of ultrasonic waves introduced to a liquid medicament, or by some other methodology described herein. Regardless of the embodiment used to form the aerosolized liquid medicament, in one example, at least 60 vol % of the aerosolized liquid medicament that is not re-liquefied and returned, e.g., recycled, to the nebulizer can be delivered into the lung airways of the user. In another example, at least 75 vol %, or even 90 vol %, of the aerosolized liquid medicament that is not recycled to the nebulizer can be delivered into the lung airways of the user. Thus, wastage can be kept to a minimum. In other examples, certain methods can include the step of releasing or equalizing gas pressure in the airflow mixing channel, if present, by a mechanism other than by inhalation of the user. The mechanism can be via a pressure release valve or an equilibration port, which can be positioned along the device from the nebulizer cup to the one-way medicament valve, e.g., on an upper portion of the nebulizer cup, on a coupler, on the airflow mixing channel. In an alternative example, the pressure release valve may also be provided by the one-way medicament valve, which can be a one-way rubber stopper valve, an inhalation oscillatory valve, or some other type of one-way valve suitable for use with the devices and assemblies of the present disclosure. In further detail, methods that utilize an aerosolized liquid medicament can include a step of mixing the aerosolized liquid medicament with air in an airflow mixing channel prior to flowing the aerosolized liquid medicament through into lung airways of a user, such as through a one-way medicament valve, which may be an inhalation oscillatory valve. In this embodiment, the airflow mixing channel can include a first inflow opening for receiving the aerosolized liquid medicament, a second inflow opening for receiving air into the airflow mixing channel, and an outflow opening fluidly coupled to a one-way medicament valve, which can be an inhalation oscillatory valve in one example. In another example, the second inflow opening can include a one-way air intake valve, which can be an inhalation oscillatory valve or a more standard one-way rubber stopper valve.

In another example, the step of flowing inhaled air or exhaled air through the inhalation oscillatory valve or the (exhalation) oscillatory valve can generate oscillation frequencies at from 6 Hz to 20 Hz, or from 10 Hz to 18 Hz, or from 12 Hz to 18 Hz, or 14 Hz to 16 Hz. Furthermore, in one example, the step of flowing exhaled air through the (exhalation) oscillatory valve can occur without allowing exhaled air to re-enter the airflow mixing channel. In one example, the method can further include adjusting the (exhalation) oscillatory valve so that the oscillation frequency is in resonance with a pulmonary resonance frequency of the user. For example, adjusting the oscillatory valve can include tilting an angle of the oscillatory valve from a neutral position to an angled position, such as by pivoting the angle of the (exhalation) oscillatory valve using a pivot joint. The pivot joint can adjust the angular relationship between the (exhalation) oscillatory valve and one or more of: i) an inhalation and expiratory mouthpiece, ii) an airflow mixing channel, or iii) a nebulizer. In another example, the (exhalation) oscillatory valve can include mechanically adjusting a counterweighted lever. For example, adjusting the counterweighted lever can include adjusting a distance between a magnet and a metallic member, wherein one of the magnet or the metallic member is associated with the counterweighted lever, and the other of the magnet or the metallic member is positioned in magnetic proximity thereto.

In specific reference to methods that utilize both an inhalation oscillatory valve and an exhalation oscillatory valve, such as shown and described with respect to the methods of FIGS. 16 and 17, in one example, a first frequency response generated by the inhalation oscillatory valve and a second frequency response generated by the exhalation oscillatory valve can be about the same. In another example, the first frequency response can be higher than the second frequency response, or alternatively, the first frequency response can be lower than the second frequency response. Thus, these methods can include adjusting the inhalation oscillatory valve, the exhalation oscillatory valve, or both to modify the first frequency response, the second frequency response, or both. Thus, adjusting can include oppositionally or separately adjusting the inhalation oscillatory valve relative to the exhalation oscillatory valve, or adjusting can include adjusting the inhalation oscillatory valve and the exhalation oscillatory valve in coordination with one another. In either example or other examples, the methods can also include flowing air and/or aerosolized liquid medicament into lung airways of the user and flowing exhaled air from the lung airways of the user, each flowing step generating a different oscillation frequency from 6 Hz to 20 Hz. The inhalation oscillatory valve, the exhalation oscillatory valve, or both can each include a weighted ball and a valve seat for receiving the weighted ball and allowing inhaled or exhaled air, respectively, to oscillate the weighted ball over or adjacent to the valve seat. In another example, the inhalation oscillatory valve, the exhalation oscillatory valve, or both can include an oscillating lever associated with a stopper and a valve seat. In still other examples, the inhalation oscillatory valve, the exhalation oscillatory valve, or both can include a chattering valve or a curved plastic tube containing a flexible hose and sound damper. The method can also include adjusting the inhalation oscillatory valve, the exhalation oscillatory valve, or both so that an inhalation oscillation frequency, an exhalation oscillation frequency, or both is in resonance with a pulmonary resonance frequency of the user. Furthermore, the inhalation oscillatory valve can be a first type of mechanical valve and the exhalation oscillatory valve can be a second type of mechanical valve, where the first type of mechanical valve is different than the second type of mechanical valve.

While the above examples, description, and drawings are illustrative of the principles of the present technology in one or more particular applications, it will be apparent to those of ordinary skill in the art that numerous modifications in form, usage and details of implementation can be made without the exercise of inventive faculty, and without departing from the principles and concepts of the present disclosure.

What is claimed is:

1. A respiratory therapy device, comprising:
   an airflow mixing channel including a first inflow opening, a second inflow opening, and an outflow opening wherein a nebulizer is fluidly coupled to or coupleable to the first inflow opening;

a one-way air intake valve fluidly coupled to the second inflow opening;

a one-way medicament valve fluidly coupled to the outflow opening; and an oscillating positive expiratory pressure assembly including a user-interface opening and an exhalation oscillatory valve configured such that the one-way medicament valve is closed during exhalation through the oscillating positive expiratory pressure assembly, the exhalation oscillatory valve comprising a valve seat and a weighted ball that provides airflow vibration as the weighted ball oscillates over or adjacent to the valve seat when actuated by the exhalation, wherein at least the valve seat of the exhalation oscillatory valve is configured to be modified with respect to the airflow mixing channel by exterior manipulation to provide a modifiable angle relationship that remains stable regardless of orientation until acted upon by a user to adjust the modifiable angle relationship by said exterior manipulation.

2. The respiratory therapy device of claim 1, wherein, when a user inhales through the user-interface opening, aerosolized liquid medicament formed at the nebulizer when connected and in operation admixes with air brought in through the one-way air intake valve to form a diluted aerosolized liquid medicament in the airflow mixing channel, wherein the diluted aerosolized liquid medicament passes through the one-way medicament valve and into the oscillating positive expiratory pressure assembly to be channeled out of the user-interface opening, and wherein, when a user exhales, exhaled air enters the user-interface opening and exits through the exhalation oscillatory valve, but does not exit through the one-way medicament valve.

3. The respiratory therapy device of claim 1, wherein the airflow mixing channel contributes to an airflow mixing channel volume defined between the nebulizer when connected, the one-way air intake valve, and the one-way medicament valve, wherein the airflow mixing channel volume is from about 15 cc to about 150 cc.

4. The respiratory therapy device of claim 3, wherein the nebulizer is present and connected to the first inflow opening and includes a nebulizer chamber having a nebulizing volume where aerosolized liquid medicament is generated which is not part of an airflow mixing channel volume, and wherein the nebulizing volume to airflow mixing channel volume is from about 1:1 to about 1:10, and wherein at least 60 vol % of the aerosolized liquid medicament that is not returned to the nebulizer is inhaled by the user.

5. The respiratory therapy device of claim 1, wherein adjusting an angle relationship between the exhalation oscillatory valve and to the airflow mixing channel modifies an oscillation frequency of the exhalation oscillatory valve.

6. The respiratory therapy device of claim 1, wherein the one-way air intake valve, the one-way medicament valve, or both includes an inhalation oscillatory valve.

7. The respiratory therapy device of claim 6, wherein the exhalation oscillatory valve and the inhalation oscillatory valve independently generate an oscillation frequency from 6 Hz to 20 Hz.

8. A method of treating a respiratory disease or condition using the respiratory therapy device of claim 6, comprising:

flowing air into lung airways of a user through an inhalation oscillatory valve actuated by user inhalation and generating a first frequency response, wherein user inhalation also draws aerosolized liquid medicament into the lungs while generating the first frequency response; and flowing exhaled air from the lung airways of the user through the exhalation oscillatory valve actuated by user exhalation and generating a second frequency response, wherein when the inhalation oscillatory valve is generating the first frequency response the exhalation oscillatory valve is closed, and when the exhalation oscillatory valve is generating the second frequency response the inhalation oscillatory valve is closed.

9. The method of claim 8, wherein the first frequency response and the second frequency response are the same, or the first frequency response is higher than the second frequency response.

10. The method of claim 8, further comprising adjusting the inhalation oscillatory valve, the exhalation oscillatory valve, or both to modify the first frequency response, the second frequency response, or both, wherein adjusting includes:

tilting an angle of the inhalation oscillatory valve, the exhalation oscillatory valve, or both from a neutral position to an angled position using a pivot joint;

oppositionally adjusting the inhalation oscillatory valve relative to the exhalation oscillatory valve; or adjusting the inhalation oscillatory valve and the exhalation oscillatory valve in coordination with one another.

11. The method of claim 8, wherein the inhalation oscillatory valve includes:

a weighted ball and a valve seat for receiving the weighted ball and to allowing inhaled or exhaled air, respectively, to oscillate the weighted ball over or adjacent to the valve seat;

an oscillating lever associated with a stopper and a valve seat; or a chattering valve or a curved plastic tube containing a flexible hose and sound damper.

12. The method of claim 8, further comprising adjusting the inhalation oscillatory valve, the exhalation oscillatory valve, or both so that an inhalation oscillation frequency, an exhalation oscillation frequency, or both is in resonance with a pulmonary resonance frequency of the user.

13. The respiratory therapy device of claim 6, wherein the one-way air intake valve includes the inhalation oscillatory valve.

14. The respiratory therapy device of claim 6, wherein the one-way medicament valve includes the inhalation oscillatory valve.

15. The respiratory therapy device of claim 1, wherein one or both of the one-way air intake valve and/or the one-way medicament valve are positioned generally downward to allow gravity to close the valves when a user is not inhaling.

16. The respiratory therapy device of claim 1, wherein the respiratory therapy device further includes the nebulizer, and the nebulizer is fluidly coupled to the to the first inflow opening and wherein the oscillating positive expiratory pressure assembly is adjustable with an oscillation frequency range of at least 10 Hz to 18 Hz.

17. The respiratory therapy device of claim 1, wherein the modifiable angle relationship that remains stable regardless of orientation is modifiable during use.

18. The respiratory therapy device of claim 1, wherein the modifiable angle relationship is provided by a pivot joint.

19. The respiratory therapy device of claim 18, wherein the pivot joint is positioned to provide pivoting of the oscillating positive expiratory pressure assembly as a whole relative to the airflow mixing channel.

20. A method of treating a respiratory disease or condition using the respiratory therapy device of claim 1, comprising:
flowing a nebulized fluid from the nebulizer through the first inflow opening and into the airflow mixing channel;
delivering the nebulized fluid to a user as a result of user inhalation by:
flowing air from outside of the respiratory therapy device through the one-way air intake valve to form a mixture of nebulized fluid and the air within the airflow mixing channel, and
flowing the mixture through the one-way medicament valve and then through the user-interface opening and lung airways of the user;
providing oscillating positive expiratory pressure therapy to the user at a first frequency as a result of exhalation through the user-interface opening and the exhalation oscillatory valve; and
adjusting the modifiable angle relationship between the valve seat and the airflow mixing channel by the external manipulation to provide oscillating positive expiratory pressure therapy to the user at a second frequency that is different than the first frequency.

21. The method of claim 20, wherein adjusting the modifiable angle relationship that remains stable regardless of orientation is carried out during use.

22. The method of claim 20, wherein adjusting the modifiable angle relationship is provided by a pivot joint.

23. The method of claim 22, wherein the pivot joint is positioned to provide pivoting of the oscillating positive expiratory pressure assembly as a whole relative to the airflow mixing channel.

* * * * *